United States Patent [19]

Weber et al.

[11] Patent Number: 5,786,174

[45] Date of Patent: Jul. 28, 1998

[54] THERMOPHILE GENE TRANSFER

[75] Inventors: J. Mark Weber; David C. Demirjian; Malcolm J. Casadaban, all of Chicago, Ill.; Nikos C. Pagratis, Boulder, Colo.; Veronika Vonstein, Chicago, Ill.

[73] Assignee: Thermogen, Inc., Chicago, Ill.

[21] Appl. No.: 790,309

[22] Filed: Jan. 28, 1997

Related U.S. Application Data

[63] Continuation of Ser. No. 265,522, Jun. 24, 1994, abandoned.

[51] Int. Cl.$^6$ .................... C12P 21/02; C12N 15/63; C07K 14/00; C07H 21/04
[52] U.S. Cl. ............... 435/69.1; 435/172.3; 530/350; 536/23.1
[58] Field of Search ................. 435/172.1, 172.3, 435/69.1; 530/350; 536/23.1

[56] References Cited

FOREIGN PATENT DOCUMENTS

0138075A1  4/1985  European Pat. Off.

OTHER PUBLICATIONS

Lasa et al., Insertional mutagenisis in the extreme thermophilic eubacteria *Themus thermophilus* HB8. Molecular Microbiology vol. 6 pages. 1555–1564, 1992.

Liao et al. Isolation of a Thermostable enzyme variant by cloning and selection in a thermophile. Proc. Natl. Acad. Sci. USA vol. 83 pp. 576–580, 1986.

Lerner et al. Sturcture of the *Bacillus subtilus* pyrimidine biosynthetic (pyr) gene cluster. J. Bacteriology vol. 169 pp. 2202–2206, 1987.

Nagahari et al. Cloning and expression of the leucine gene from *Thermus thermophilus* in *Escherichia coli*. Gene vol. 10 pp. 137–145, 1980.

Lerner et al. J. Bacteriology 169 2202–2206 (1987) Structure of the *Bacillus subtilis* Pyrimidine Biosynthetic . . . .

Liao et al. Proc. Natl. Acad. Sci. USA 83 576–580 (1986) Isolation of a Thermostable Enzyme Varaint by Cloning and Selection . . . .

Lasa et al. Molecular Microbiology 6 1555–1564 (1992) Insertional Mutagenesis in the Extreme Thermophilic eubacteria . . . .

Nagahari et al. Gene 10 137–145 (1980) Cloning and Expression of the Leucine Gene from Thermus . . . .

Sen & Oriel (1990) Transfer to transposon Tn916 from *Bacillus subtilis* to *Thermus aquaticus*, FEMS Microbiology Letters 67:131–134.

Koyama et al. (1990) A plasmid vector for an extreme thermophile, *Thermus thermophilus*, FEMS Microbiology Letters 72:97–102.

Koyama & Furukawa (1990) Cloning and Sequence Analysis of Tryptophan Synthetase Genes of an Extreme Thermophile, *Thermus thermophilus* HB27: Plasmid Transfer from Replica–Plated *Escherichia coli* Recombinant Colonies to Competent *T. thermophilus* Cells, *J. of Bacteriology* 172:3490–3495.

Koyama et al. (1986) Genetic Transformation of the Extreme Thermophile *Thermus thermophilus* and of Other Thermus spp., *J. Bacteriology* 166:338–340.

Borges & Bergquist (1993) Genomic Restriction map of the Extremely Thermophilic Bacterium *Thermus thermophilus* HB8, *J. Bacteriology* 175:103–110.

Matsumura et al. (1984) Enzymatic and Nucleotide Sequence Studies of a Kanamycin–Inactivating Enzyme Encoded by a Plasmid from Thermophilic Bacilli in Comparison with That encoded by Plasmid pUB110, *J. of Bacteriology* 160:413–420.

Matsumura & Aiba (1985) Screening of Thermostable Mutant of Kanamycin Nucleotidyltransferase by the Use of a Transformaion System for a Thermophile, *Bacillus stearothermophilus, J. of Biological Chemistry* 260:15289–15303.

Matsumura et al. (1986) Cumulative effect of intragenic amino–acid replacements on the thermostability of a protein, *Nature* 323:356–358.

Liao et al. (1986) Isolation of a thermostable enzyme variant by cloning and selection in a thermophile, *PNAS USA* 83:576–580.

Lasa et al. (1992a) Development of Thermus–Escherichia Shuttle Vectors and Their Use for Expression of the *Clostridium thermocellum* celA Gene in *Thermus thermophilus, J. of Bacteriology* 174:6424–6431.

Faraldo et al. (1992) Sequence of the S–Layer Gene of *Thermus thermophilus* HB8 and Functionality of its Promoter in *Escherichia coli, J. of Bacteriology* 174:7458–7462.

Mather & Fee (1992) Development of Plasmid Cloning Vectors for *Thermus thermophilus* HB8: Expression of a Heterologous, Plasmid–Borne Kanamycin Nucleotidyltransferase Gene, *Applied and Envior. Microbiology* 58:421–425.

Nagahari et al., (1980) Cloning and expression of the leucine gene from *Thermus thermophilus in Escherichia coli, Gene* 10:137–145.

Tanaka et al. (1981) Cloning of 3–Isopropylmalate Dehydrogenase Gene of an Extreme Thermophile and Partial Purification of the Gene Product, *Biochem.* 89:677–682.

(List continued on next page.)

*Primary Examiner*—James Ketter
*Assistant Examiner*—John S. Brusca
*Attorney, Agent, or Firm*—McDonnell Boehnen Hulbert & Berghoff

[57] ABSTRACT

We have developed a new gene transfer system for extreme thermophiles of the genus Thermus, including *Thermus flavus*, using a chromosomal gene, and a thermostable derivative of the kanamycin-resistance gene (kan$^{tr2}$). A plasmid mediated gene-replacement process is used to insert it into the chromosome resulting in the production of Leu$^-$ Km$^r$ transformants. This system not only allows stable, single-copy gene insertion into the chromosome of an extreme thermophile, but can be used in the thermo-genetic process described here to generate thermo-stabilized enzymes and proteins for industrial processes. This host-vector environment makes it possible to generate further thermo-stabilizing mutations in the kan gene beyond those levels previously reported.

5 Claims, 8 Drawing Sheets

OTHER PUBLICATIONS

Croft et al. (1987) Expression of leucine genes from an extremely thermophilic bacterium in *Escherichia coli*, Molec. Gen. Genet. 210:490–497.

Yamada et al. (1990) Purification, Catalytic Properties, and Thermal Stability of Threo–Ds–3–Isopropylmalate Dehydrogenase Coded by euB Gene form an Extreme Thermophile, *Thermus thermophilus* Strain HB8, *J. Biochem.* 108:449–456.

Kirino & Oshima (1991) Molecular Cloning and Nucleotide Sequence of 3–Isopropylmalate Dehydrogenase Gene (leuB) from an Extreme Thermophile, *Thermus aquaticus* YT–1, *J. Biochem.* 109:852–857.

Imada et al. (1991) Three–dimensional Structure of a Highly Thermostable Enzyme, 3–Isopropylmalate Dehydrogenase of *Thermus thermophilus* at 2.2 Å Resolution, *J. Mol. Bio.* 222:725–738.

Onodera et al. (1991) Crystallization and Preliminary X–Ray Studies of a *Bacillus subtilis* and *Thermus thermophilus* HB8 Chimeric 3–Isopropylmalate Dehydrogenase, *J. Biochem.* 109:1–2.

Lacey, R. W. and I. Chopra (1974) Genetic studies of a multiresistant strain of *Staphylococcus aureus*. *J. Med. Microbiol.* 7: 285–297.

pVUF10.5

```
       KpnI (1)
   1   GGTACCGGGA GGGTCCCTGG AGCCGGGTGG GGATGGTGGT GGGGGCCACC TACCCGGGGG CCGTGGCTCG
  71   GGTGCGGGAA AGGGCGCCCC ACGCCCCCCT CCTCCTCCCC GGCGTGGGGG CCCAGGGGGG GAGGCCCTCA
 141   AGGGGGAGGG GCTTCTTTTC GCGGCGAGCC GGGCCCTCTA CTACCCTGGG GGAAGGCCGG ACCTAAAGGC
 211   CGCCCTGGAG GCGGCGGAGG CCCTCTTGAA GGCTCTGGTA GAGTAGGGGG G ATG GAC GTC CTG GAG
                                                              1▶Met Asp Val Leu Glu

277   CTT TAC CGG AGG ACG GGG GCT CTT CTA GAG GGC CAC TTC CTC CTG CGC TCG GGG ATG
   6▶  Leu Tyr Arg Arg Thr Gly Ala Leu Leu Glu Gly His Phe Leu Leu Arg Ser Gly Met

334   CAC TCC CCC TTC TTT TTG CAG TCG GCG GCC CTC CTC CAG CAT CCC CTT TAC GCC GAG
  25▶  His Ser Pro Phe Phe Leu Gln Ser Ala Ala Leu Leu Gln His Pro Leu Tyr Ala Glu
                                                                   TthIII (436)

391   GCC GTG GGG GAG GCT TTG GGA AAG CTC TTT GAG GAC GAG AAG GTG GAC TTC GTC ATC
  44▶  Ala Val Gly Glu Ala Leu Gly Lys Leu Phe Glu Asp Glu Lys Val Asp Phe Val Ile

448   GCC CCG GCC ATC GGG GGC GTG GTC CTT TCC TTC GTG GTG GCG AAG GCC TCG GGC CCG
  63▶  Ala Pro Ala Ile Gly Gly Val Val Leu Ser Phe Val Val Ala Lys Ala Ser Gly Pro

505   GGC CCT CTT CGC CGA GAA GGA CGG AAG GGG AGG GAT GCT CAT CCG CAA GGG GCT CAC
  82▶  Gly Pro Leu Arg Arg Glu Gly Arg Lys Gly Arg Asp Ala His Pro Gln Gly Ala His

562   CGT GAA CCC GGG CGA CGC TTC TTG GCG GTG GAG GAC GTG GTA ACC ACC GGG GAG AGC
 101▶  Arg Glu Pro Gly Arg Arg Phe Leu Ala Val Glu Asp Val Val Thr Thr Gly Glu Ser
                           Sau3AI (630)

619   GTC CGC AAG GCG ATC CGG GCG GCG GAG GCC CGG GGC GGG GTT TTG GTG GGC GTG GGG
 120▶  Val Arg Lys Ala Ile Arg Ala Ala Glu Ala Arg Gly Gly Val Leu Val Gly Val Gly

676   GCC ATC GTG GAC CGG AGC GGG GGC AGG GCG GCC TTC GGC GTG CCC TTC CGC GCC CTC
 139▶  Ala Ile Val Asp Arg Ser Gly Gly Arg Ala Ala Phe Gly Val Pro Phe Arg Ala Leu

733   CTC GCC TTG GAG GTT CCC CAG TAT CCC GAG GAG GCC TGC CCC CTC TGC CGG GAG GGG
 158▶  Leu Ala Leu Glu Val Pro Gln Tyr Pro Glu Glu Ala Cys Pro Leu Cys Arg Glu Gly

790   GTG CCC TTG GAG GAG GTT TAG GGTGCGCTTC CTCGCTGCCC TTCTTCTCGG CCTTTTCTCC
 177▶  Val Pro Leu Glu Glu Val ▪▪▪

851   CTGGCCCTCG CGGCCCCGGA GGAGGCCGCG AGGGAGACCG TCGCCCGGTG GCTCAGGGGG GAGCTCTCCC
              Xhol (926)                                    Xhol (971)
 921   CGAGCCTCGA GGAGGTCCTT AGGGCCCCTC CGGAGGAGGC CCCGAGGCTC CTCGAGCGTT CGCCCTCTTC
 991   CCCCCGCCCC CCGATGGGCT TACCGTCAAC CTGGAAAGCC CCGAGGTCGA GGGGAACCGG GTCTCCTTCC
1061   CGGCCGCCCT CGGGGAGGAG GTGGGGGAGG TGGTGGTGGT CCTGGAAGGG GGGGAGGCCA GGCGGGTCTA
1131   CTTCCGCCCC GAGGCTCGGG TGCCCGCCTA CCTCCTCACG CCCCTCGCGG GCTTTGGGTT TTTCCTCCTC
1201   TCCCTCTTTT GGGTCTTCCT CCTCCTCAGG CCCTCCCCCT TCCGGCCTG GCTTCTTGAG GCCTGGGCCT
1271   TGGTCCGGTC CCAGAGGGGC CTTTACCTCT TCACCAACCT CTTCCTCTAC GGCCTATTCG CCCTGGGGAG
1341   CCTTCTCGCC TACGCCATGC CCGAGCTCGC CCGGGCGGTG CAGGTCCTCT TCGGGGCGC CTTGGAGGCC
1411   ATCGGCCTCC AGGAGGCGGT GGGGAAGGGC GTTTTGGTCC TCGCTGGGGT CATCTTTCAC TGGAATTTCA
1481   GCCAGGGGCT TTTCCTCACA GGGCTCCTTC CCGCCTTGCT CTTGGGGGTT CCTGTGCTCC TCCTCAACGC
1551   CCTCCGCTAC TTCGCTTCGT TCGCCCTCTC CCCGGCCCTT CTGGGAAGCG CCTTCCTCTT CCACCTGCCC
1621   ACCCTTCTTT TGGAGCTTCA GGCCTACATC CTCGTCACTT CGGCGGGCTC GTCCTCCTCG CCCGGGTGGC
            KpnI (1702)
1691   CGGGGGGCAG GGGTACC
```

Fig. 2

THERMOPHILE GENE TRANSFER

This application is a continuation of application Ser. No. 08/265,522, filed on 24 Jun., 1994, now abandoned.

FIELD OF THE INVENTION

The instant invention is related to the field of thermophilic microorganisms the stable gene transfection in and protein expression thereof, and in the genetic thermostabilization of proteins.

BACKGROUND OF THE INVENTION

Extreme thermophilic microorganisms such as Thermus, thrive in high-temperature environments that are lethal to other known forms of life. Fortunately, apart from their higher growth temperature requirement, they can be handled in the laboratory much like E. coli. Enzymes from thermophiles are thermostable and are therefore used in industrial processes that benefit from a high reaction temperature. Also, these enzymes have become widely used in molecular genetic research, for example, in the development and application of the polymerase chain reaction (PCR).

One area of particular interest in the field of thermophile research is the determination of molecular mechanisms underlying enzymatic thermostability. Ultimately, a better understanding of this phenomenon will allow mesophilic proteins to be rationally converted to thermostable proteins for industrial applications. Many groups have attempted to engineer thermostability in proteins through in vitro rational design approaches (Perry and Wetzel, 1984, *Science* 226:555–557; Sauer, et al., 1986, *Biochemistry* 25:5992-8; Pantoliano, et al., 1987, *Biochemistry* 26:2077-82; Meng, et al., 1993, *Bio/Technology* 11:1157–1161) or through homology comparison and domain fusion of related proteins (Onodera, et al., 1991, *J Biochem* 109:1-2; Barany, et al., 1992, *Gene* 112:3–12; Politz, et al., 1993, *Eur J Biochem* 216:829-34; Lee, et al., 1993, *J Bacteriol* 175:5890-8). These approaches, however, often require either a three dimensional protein structure or a series of related proteins. For proteins which have not been well characterized, random mutagenesis can be a powerful tool if the proper selection or screen can be applied (Matsumura and Aiba, 1985, *J Biol Chem* 260:15298–15303; Liao, et al., 1986, *Proc Natl Acad Sci USA* 83:576–580; Kajiyama and Nakano, 1993, *Biochemistry* 32:13795-9; Arnold, 1993, *Faseb J* 7:744-9). The instant invention provides a genetic process for the insertion of exogenous protein coding sequences into, and direct selection of thermostable variants of mesophilic enzymes. Other "thermo-genetic" processes, were attempted by Liao (Liao et al., 1986, *Proc. Natl. Acad. Sci. USA* 83:576–580), EP Patent application 0 138 075, and by Matsumura (Matsumura et al., 1985, *J Biol. Chem.* 260:15298–15303).

The concept of "thermo-genetics" consists of a method for introducing a gene of interest into a thermophile followed by a temperature-shift to select for temperature-resistant mutations in the corresponding protein of interest. The model thermo-genetic systems (EP Patent application 0 138 075; Matsumura, 1985; Liao, 1986) used the mesophilic kanamycin-resistance gene (kan) on a multicopy plasmid in the moderate thermophile *Bacillus stearothermophilus*. The kan gene was first introduced into *B. stearothermophilus* at the lowest permissible temperature of growth, 47° C. Two consecutive thermal shifts, first to 63° C. and then to 69° C., resulted in two corresponding thermo-stabilizing mutations, producing the double mutant allele, designated here as kan$^{tr2}$. At this point the upper limit for permissible growth had been reached, creating a barrier to further selections for temperature-resistant mutations. Matsumura also performed a related series of experiments generating the same two mutants in parallel (Matsumura et al., 1986, *Nature* 323:356–358) and later showed they could be combined with an additive result.

While other host-vector systems have been developed for *Thermus thermophilus*, a closely related thermophile, they all have deficiencies in their ability to be used in a thermostabilization process and in stable integration of exogenous genes into Thermus. Two plasmid-based systems use multicopy plasmids with an unstable copy number which can interfere with mutant selection (Mather and Fee, 1992, *Appl Environ Microbiol* 58:421–425; Lasa, et al., 1992, *J Bacteriol* 174:6424–6431). The multicopy nature of these systems do not ideally lend themselves to thermostabilization of genes since many copies of the gene of interest are present, and can mask any desired mutations which may occur. In addition, reports with plasmid-based systems in Thermus indicate that the plasmids are very unstable, that copy number varies widely, and that gene duplication and amplification can occur, making them very difficult to use. Another approach which used an insertional mutagenesis system was developed by Lasa et. al. (Lasa, et al, 1992, *Molec Microbiol* 6:1555–1564) but unfortunately caused a debilitating phenotype in the host organism.

In Lasa's insertional mutagenesis system, the kan$^{tr2}$ was inserted in single copy into a highly-expressed (slpA) region of the chromosome for use in chromosomal insertion strategy (Lasa et al. 1992a, J. Molec. Microbiol. 6, 1555–1564; Lasa et al. 1992b, J. Bacteriol. 174, 6424–6431). This system used the slpA gene which codes for an abundant cell surface protein and therefore was likely to be highly expressed. A high expression site was originally a logical choice for testing the feasibility of a single-copy system.

Unfortunately, insertion into slpA results in debilitating growth and morphology phenotypes making it difficult to use the plasmid system.

References which define the background of the invention, but which are not necessarily prior art to the instant invention are as follows. The references cited herein, above and below are hereby incorporated by reference in their entirety.

Sen & Oriel (1990) Transfer of transposon Tn916 from *Bacillus subtilis* to *Thermus aquaticus*, *FEMS Microbiology Letters* 67:131–134, teach the use of the Streptococcus transposon Tn916, carrying tetracycline resistance for conjugal transfer into *Thermus aquaticus* via *Bacillus subtilis*. This was found to be effective at 48° C. and 55° C. The actual insertion site is unknown.

Koyama et al. (1990) A plasmid vector for an extreme thermophile, *Thermus thermophilus*, *FEMS Microbiology Letters* 72:97–102, teach a Thermus-*E. coli* shuttle vector carrying a tryptophan synthetase gene (trpB). This cryptic plasmid pTT8, was able to transform *Thermus thermophilus*. The authors point out that a plasmid vector carrying trpBA was not suitable for selection since the cloned DNA fragment recombined with the chromosomal counterpart at high frequency.

Koyama & Furukawa (1990) Cloning and Sequence Analysis of Tryptophan Synthetase Genes of an Extreme Thermophile, *Thermus thermophilus* HB27: Plasmid Transfer from Replica-Plated *Escherichia coli* Recombinant Colonies to Competent *T. thermophilus* Cells, *J. of Bacteriology* 172:3490–3495, disclose nucleotide sequences for trpBA genes, their use in plasmids and expression in *E. coli* under the control of the lac promoter.

Koyama et al. (1986) Genetic Transformation of the Extreme Thermophile *Thermus thermophilus* and of Other Thermus spp., *J. of Bacteriology* 166:338–340, discuss the conditions for optimal transformation with exogenous DNA. The use of *Thermus thermophilus* HB27 did not require chemical treatment to induce competence, although the addition of $Ca^{+2}$ and $Mg^{+2}$ was optimal. The optimal conditions were found to be 70° C. with a 60 minute incubation, pH 6 to 9.

Borges & Bergquist (1993) Genomic Restriction Map of the Extremely Thermophilic Bacterium *Thermus thermophilus* HB8, *J. of Bacteriology* 175:103–110, teach the use of *Thermus thermophilus* HB8, which carries two cryptic plasmids, pTT8 and pVV8 was examined. A genomic restriction map was generated, 16 genes located on the map.

Matsumura et al (1984) Enzymatic and Nucleotide Sequence Studies of a Kanamycin-Inactivating Enzyme Encoded by a Plasmid from Thermophilic Bacilli in Comparison with That encoded by Plasmid pUB110, *J. of Bacteriology* 160:413–420, teach the a Kanamycin resistance gene from a thermophilic bacteria plasmid pTB913 was found to differ by only one base pair in the middle of the gene, from that of a mesophilic *Staphylococcus aureus* plasmid pUB110. The change was a cytosine(pUB) to adenine(pTB) at base position +389, which led to a threonine to lysine change at position 130.

Matsumura & Aiba (1985) Screening for Thermostable Mutant of Kanamycin Nucleotidyltransferase by the Use of a Transformation System for a Thermophile, *Bacillus stearothermophilus, J. of Biological Chemistry* 260:15289–15303, disclose a structural gene for kanamycin nucleotidyltransferase that was cloned into the single-stranded bacteriophage M13 and then subjected to hydroxylamine mutagenesis. The mutagenized gene was then recloned into a vector plasmid pTB922 and used to transform *Bacillus stearothermophilus* to select for improved enzyme thermostability. A temperature shift from 55° C. to 61° C. was used for selection. Two types of mutations were found, at position 80 an aspartate to tryptophan, and at position 130 a threonine to lysine. These were found stable up to 65° C. The kan gene came from pUB110.

Matsumura et al. (1986) Cumulative effect of intragenic amino-acid replacements on the thermostability of a protein, *Nature* 323:356–358, teach improved thermostability of kanamycin nucleotidyltransferase (KNTase) was shown to be due to the Asp80 to Tyr(Y80) and Thr130 to Lys(K130) mutation. This also correlated with increased resistance to proteolysis. Catalytic activity was also measured at various temperatures and it was found that the activities deteriorate slightly as thermostability increases, but the optimal temperature is shifted upwards. It is thought that increased hydrogen bonding and hydrophobic interactions act as forces to stabilize the enzyme.

Liao et al. (1986) Isolation of a thermostable enzyme variant by cloning and selection in a thermophile, *PNAS USA* 83:576–580, teach a kan gene transferred via shuttle vector into *B. stearothermophilus* and selected for at 63° C. The shuttle plasmid was passed through the *E. coli* mutD5 mutator strain and introduced by transformation. The vector combined the kan gene from pUB110 with a putative thermostable origin of replication from pBST1, isolated from a kanamycin-sensitive strain NRRL1102.

Lasa et al. (1992a) Development of Thermus-Escherichia Shuttle Vectors and Their Use for Expression of the *Clostridium thermocellum celA* Gene in *Thermus thermophilus*, *J. of Bacteriology* 174:6424–6431, teach the self-selection of undescribed origins of replication from cryptic plasmids from uncharacterized Thermus spp. and *Thermus aquaticus* are isolated and cloned into *E. coli* vectors. Plasmids were constructed with these origins, pLU1 to pLU4 from *T. aquaticus*, and pMY1 to pMY3 from Thermus spp. The plasmids then had a modified form of the cellulase gene (celA) from *Clostridium thermocellum* and were expressed in *E. coli* with the signal peptide from the S-layer gene from *T. thermophilus*. Transformation back into *T. thermophilus* allowed for expression at 70° C.

Lasa et al. (1992b) Insertional mutagenesis in the extreme thermophilic eubacteria *Thermus thermophilus* HB8, *Molecular Microbiology* 6:1555–1564, teach the transcription and translation signals from the slpA gene from *Thermus thermophilus* HB8 used to express a thermostable kan gene. After 48 hours at 70° C., two isolates were obtained.

Faraldo et al. (1992) Sequence of the S-Layer Gene of *Thermus thermophilus* HB8 and Functionality of Its Promoter in *Escherichia coli, J. of Bacteriology* 174:7458–7462, disclose the S-layer gene slpA , sequenced and the function in *E. coli* described.

Mather & Fee (1992) Development of Plasmid Cloning Vectors for *Thermus thermophilus* HB8: Expression of a Heterologous, Plasmid-Borne Kanamycin Nucleotidyltransferase Gene, *Applied and Envior. Microbiology* 58:421–425

A plasmid cloning vector is disclosed which uses the kan gene inserted randomly into a cryptic multicopy plasmid (pTT8) isolated from *T. thermophilus*.

Nagahari et al. (1980) Cloning and expression of the leucine gene from *Thermus thermophilus* in *Escherichia coli, Gene* 10:137–145, describe the *Thermus thermophilus* leu locus cloned into *E. coli* and expressed. The plasmid pBR322-T.leu hybrid plasmid was constructed to encode the β-IPM dehydrogenase activity (leuB), the optimal temperature of which was 80° C. Experiments suggest that there is a promoter that may be used in *E. coli*.

Tanaka et al. (1981) Cloning of 3-Isopropylmalate Dehydrogenase Gene of an Extreme Thermophile and Partial Purification of the Gene Product, *Biochem.* 89:677–682, demonstrate the cloning into *E. coli*, protein production, and heat-treatment purification of *Thermus thermophilus* 3-IPM.

Croft et al. (1987) Expression of leucine genes from an extremely thermophilic bacterium in *Escherichia coli*, *Molec. Gen. Genet.* 210:490–497, describe the promoter for the leu BCD genes in *Thermus thermophilus* HB8. The structural similarity with known leu genes is examined. Thermus DNA failed to complement *E. coli* leuA mutants. Perhaps leuA is not functional.

Yamada et al (1990) Purification, Catalytic Properties, and Thermal Stability of Threo-Ds-3-Isopropylmalate Dehydrogenase Coded by leuB Gene form an Extreme Thermophile, *Thermus thermophilus* Strain HB8, *J. Biochem.* 108:449–456, demonstrate the product of leuB from *Thermus thermophhilus* as expressed in *E. coli* by plasmid. The enzyme was purified using heat treatment.

Kirino & Oshima (1991) Molecular Cloning and Nucleotide Sequence of 3-Isopropylmalate Dehydrogenase Gene (leuB) from an Extreme Thermophile, *Thermus aquaticus* YT-1, *J. Biochem.* 109:852–857, here the gene encoding *T. aquaticus* leuB was cloned into *E. coli* and expressed.

Imada et al. (1991) Three-dimensional Structure of a Highly Thermostable Enzyme, 3-Isopropylmalate Dehydrogenase of *Thermus thermophilus* at 2.2 Å Resolution, *J. Mol. Bio.* 222:725–738, desribe the 3D structure of IPMDH from *Thermus thermophilus* has been determined and refined to 2.2 Å resolution. The dimeric form of IPMDH is crucial to function.

Onodera et al. (1991) Crystallization and Preliminary X-Ray Studies of a *Bacillus subtilis* and *Thermus thermophilus* HB8 Chimeric 3-Isopropylmalate Dehydrogenase. *J. Biochem.* 109:1–2, teach a chimeric gene fusing the *Bacillus subtilis* and *Thermus thermophilus* genes encoding for IPMDH, cloned into *E. coli*.

Liao et al., European Patent Application 0 138 075 A1 published 24.04.85, discloses the use of plasmids for transforming thermophilic bacteria. A method for isolating thermostable promoters, a method for selecting thermostable variants of gene products of cloned genes in thermophilic hosts using the plasmids of the invention. Such plasmids as:

pBST1, 80 kb cryptic single copy plasmid isolated from *B. stearothermophilus* at 70° C.

pBST2, 1.4 kb, $O_R$ of pBST1 & $kan^R$ of pUB110, grows at 70° C., kan up to 47° C. 3 copy.

pBST2-6, pBST2 with oligonucleotide linker to form HindIII site, kan <55° C.

pBST2-6TK, variant of pBST2-6, kan activity up to 66° C.

pSHW9, chloramphenicol$^R$ CATfrom pC194, in pBR322, amp$^R$, pBR322 OR+pC194.

pBST8, pBST2-6+pSHW9, "Shuttle vector"

pCV1, pSHW9 with promoter substituted by polylinker site.

pCV3, pCV1 missing NarI site.

pBST110, pCV3+pBST2-6, shuttle vector, no CAT production.

pRMS10, shotgun clone into pBST110, a promoter from *B. stearothermophilus*.

Lacey, R. W. and I. Chopra. Genetic studies of a multiresistant strain of *Staphylococcus aureus*. *J. Med. Microbiol.* 7:285–297, 1974, discribes plasmid pUB110 which contains the Kan gene.

BRIEF DESCRIPTION OF THE DRAWINGS

FIG. 2 is the nucleic acid sequence (SEQ ID NO:1) of the pyrE gene from *T. flavus*. The DNA sequence which complements an *E. coli* pyrE mutation and the open reading frame thought to encode the pyrE gene of *Thermus flavus* are shown. The standard three-letter amino acid sequences are used.

SUMMARY OF THE INVENTION

Figure 1:
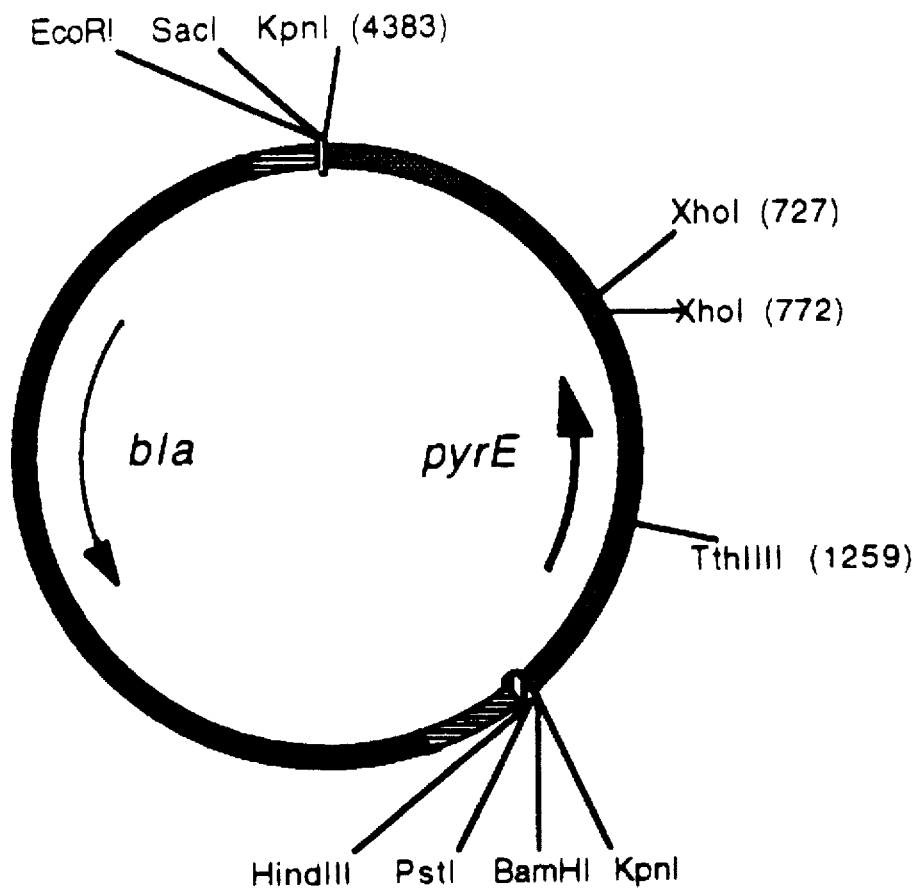
FIG. 1 is the physical map of pVUF10.5 composed of the KpnI fragment from pVUF10 containing pyrE gene (grey) cloned into the KpnI site of pUC19 (black). The location and direction of the bla gene conferring ampicillin resistance and the pyrE gene from *T. flavus* are shown with arrows.

The instant invention is directed to recombinant DNA which contain a DNA fragment isolated from a Thermus strain, such as *Thermus flavus*, which contain a site for insertion of a coding sequence for a heterologous protein, and which contain a coding sequence which directs the insertion of the DNA fragment into a regulated region of a Thermus chromosome so that the expression of the exogenous protein is regulated by the Thermus chromosome. In a prefered embodiment the Thermus strain is *Thermus flavus*.

In one embodiment, a recombinant DNA as above, preferably contains a 3 kb DNA fragment isolated from Thermus which complements a leuB mutation in *E coli* MC1066, or equivalents thereof.

In another embodiment, a recombinant DNA as above, preferably contains a 1.7 kb fragment isolated from Thermus which complements a pyrE mutation in *E. coli* BW322, or equivalents thereof.

In a preferred embodiment, a recombinant DNA as above, contains a DNA fragment corresponding to the leuB gene locus isolated from Thermus that contains an exogenous DNA insert which is capable of being expressed under the control of the leuB regulatory signals.

The instant invention and the compositions which flow naturally from the teachings of the instant invention encompass methods of inserting an exogenous DNA sequence into a targeted chromosomal DNA region of a thermophilic microorganism comprising the steps of; constructing a plasmid vector which contains a targeting DNA sequence which corresponds to the targeted chromosomal DNA, inserting into the plasmid vector targeting DNA sequence an exogenous DNA, the insertion of which interferes with the normal expression of the targeting DNA sequence, transforming a host cell with the plasmid vector, selecting stable transformants by screening at temperatures above 55° C., confirming gene-replacements by southern blotting.

The instant invention also contemplates the above method where the insertion does not result from a interruption of the gene function. Also encompassed are fusion proteins.

Thus the instant invention also encompasses a host cell which has been transformed by the methods of the instant invention. Specific strains which have been transformed by the methods of the instant invention include *T. flavus* AT62.

In a particular embodiment, the methods of the instant invention encompass where the exogenous DNA sequence encodes the kan gene.

Further, the methods of the instant invention encompass where the targeting DNA sequence and the targeted chromosomal DNA sequence is the leuB gene.

The instant invention also encompasses methods of evolving thermostable proteins which comprises using cells transformed by the methods and compositions of the instant invention, and subjecting them to elevated temperatures for selection of mutated thermostable proteins. In a prefered embodiment, the compositions are stable cells which have been transformed by the methods of the instant invention, to express a heterologous protein.

Thus the instant invention embodies a recombinant DNA which contains a DNA fragment isolated from Thermus, which DNA fragment contains a site for insertion of an exogenous DNA coding sequence, and which DNA fragment contains a DNA coding sequence which directs the targeted insertion of the DNA fragment into a region of a Thermus chromosome, such that the exogenous protein is expressable.

The instant invention further provides for a recombinant DNA as above which contains a DNA fragment isolated from *Thermus flavus*, which complements a leuB mutation in *E. coli* MC1066. In the prefered embodiment the instant invention provides for a recombinant DNA as above which contains a 3 kb DNA fragment isolated from *Thermus flavus* which complements a leuB mutation in *E. coli* MC1066.

Further the instant invention embodies a recombinant DNA which contains a DNA fragment isolated from *Thermus flavus* which complements the pyrE gene, which is capable of being expressed under the control of Thermus regulatory signals.

The instant invention also embodies a recombinant DNA which contains a DNA fragment corresponding to the leuB gene isolated from Thermus that contains an exogenous DNA insert which is capable of being expressed under the control of leuB regulatory signals.

In addition the instant invention embodies a recombinant DNA which contains a DNA fragment corresponding to the pyrE gene isolated from Thermus that contains an exogenous DNA insert which is capable of being expressed under the control of pyrE regulatory signals.

The instant invention also embodies the regulation of expression by other signals.

The instant invention provides methods of isolating proteins comprising growing cells in media and isolating protein, wherein said cells were transformed with a vector, by the insertion of a targeting DNA sequence from said vector into a corresponding targeted chromosomal DNA region of a thermophilic microorganism, wherein said targeting DNA sequence contains an exogenous DNA sequence, where the insertion of the exogenous DNA sequence interferes with the normal expression of the targeting DNA sequence, and said exogenous DNA sequence encodes for the desired protein, where the expression of the protein is under the regulation of a chromosome.

In preferred embodiments this method is used where the exogenous DNA sequence encodes the kan gene, where the targeting DNA sequence and the targeted chromosomal DNA sequence is the leuB gene, and where the targeting DNA sequence and the targeted chromosomal DNA sequence is the pyrE gene.

The instant invention also encompasses methods of producing a stable host cell transformant which produces a protein comprising, growing host cells and selecting for a stable host cell transformant where the host cells have been transformed with a vector, where said vector transforms the host cell by inserting a targeting DNA sequence into a targeted chromosomal DNA region of a thermophilic microorganism, which targeting DNA sequence contains an exogenous DNA sequence, which exogenous DNA sequence interferes with the normal expression of the targeting DNA sequence, and the expression of the exogenous DNA sequence is regulated by the chromosome.

In preferred embodiments this method is used where the exogenous DNA sequence encodes the kan gene, where the targeting DNA sequence and the targeted chromosomal DNA sequence is the leuB gene, where the targeting DNA sequence and the targeted chromosomal DNA sequence is the pyrE gene.

Thus the instant invention also provides for methods of evolving thermostable proteins which comprises subjecting host cells to elevated temperatures for selection of mutated thermostable proteins in a step-wise fashion, where said host cells were produced by, growing host cells and selecting for a stable host cell transformant, where the host cells have been transformed with a vector, where said vector transforms the host cell by inserting a targeting DNA sequence into a targeted chromosomal DNA region of a thermophilic microorganism, which targeting DNA sequence contains an exogenous DNA sequence, which exogenous DNA sequence interferes with the normal expression of the targeting DNA sequence, and the expression of the exogenous DNA sequence is regulated by the chromosome.

In preferred embodiments, this is done where the exogenous DNA sequence encodes the kan gene, where the targeting DNA sequence and the targeted chromosomal DNA sequence is the leuB gene, and where the targeting DNA sequence and the targeted chromosomal DNA sequence is the pyrE gene.

The instant invention also further provides for a host cell which has been produced by the above methods, and protein which has been isolated and/or produced by the above methods.

In one embodiment the invention encompasses a cell which is a strain of *Thermus flavus*, which has been transformed by plasmid vector pTG101.

In one embodiment the instant invention encompasses a nucleic acid sequence comprising the sequence which encodes the *Thermus flavus* pyrE gene (SEQ ID. 1). Which is useful as an additional target for specific chromosomal integration in Thermus. Further the instant invention provides for the protein translated from the pyrE gene which is a polypeptide comprising the amino acid sequence of pyrE (SEQ. ID. 2) and is a thermostable dehydrogenase and is useful for synthetic applications.

Other embodiments of the methods and compositions of the instant invention will be readily apparent to one of ordinary skill in the art from the teachings of the instant disclosure, which would allow such a person to practice the methods of the instant invention.

DETAILED DESCRIPTION OF THE INVENTION

The presently available thermogenetic systems offer a range of temperatures at which selection may be carried out. While these temperatures were reasonably interesting for academic work, they were not sufficient for the system to be useful to thermostabilize enzymes and proteins at the levels needed in commercial applications. There was a limitation to the process because of the upper growth temperature of the host organism. An improved thermogenetic system would allow for selection at higher temperatures and a wider range of temperatures to provide solutions to the limitations of the previous efforts.

To circumvent the limitation of temperature, we chose to work with a more extreme thermophile, *Thermus flavus*, which has an upper growth limit, at least 10° C. higher than *B. stearothermophilus*.

Starting with the double thermo-stabilized $kan^{r2}$ gene (provided by H. Liao) we teach a gene transfer system using chromosomal integration. In our system, however, we inserted $kan^{r2}$ into the *Thermus flavus* leuB gene rather than into the slpA gene of *Thermus thermophilus* (Lasa et al., 1992). LeuB has been well-characterized in related organisms, it was also predicted to have a benign mutant phenotype. Since $kan^{r2}$ is selectable when inserted into a common metabolic gene like leuB and at a relatively low expression level, it is possible that it will also be selectable in many other sites as well. This opens the possibility of using $kan^{r2}$ for mutational analysis of the entire Thermus chromosome. We have also cloned two other metabolic genes of *Thermus flavus*, pyrE and his, which will be useful markers in chromosomal insertion systems. Thus the instant invention encompasses the use of the methods of the instant invention for the directed insertion of DNA sequences into other metabolic genes of *T. flavus*.

The instant invention circumvents the problems encountered by other groups and provides a host-vector system that would lend itself to further thermogenetic selections. The instant invention demonstrates that a low- or regulatable-expression system has significant advantages over the high expression system.

The teachings of the instant specification provide a new integrative gene transfer system based on the leuB gene insertion site, and teach how this system enables one to perform further thermo-genetic selections on the $kan^{r2}$ gene. Surprisingly, due to the unique properties of our system, the observed potential for thermo-genetic selections with our new system is significantly greater than the additional 10° C. expected from the new host.

We have been able to obtain mutants in $kan^{r2}$ that were able to grow at 65° C. having varying degrees of linkage between Leu⁻ and the $kan^{r2+}$ phenotypes. The differences in linkage indicated that different types of mutations were probably obtained. Mutations showing a high linkage would have the greatest probability of being true thermo-stabilizing mutations in $kan^{r2}$; low linkage could indicate mutations in the leuB regulatory region (high-expression mutants) or in other genes controlling the level of kanamycin in the cell.

The instant specification teaches a new integrative gene transfer system in the extreme thermophile *Thermus flavus* using $kan^{r2}$ as the selectable marker and leuB as the site of insertion. This system is useful for performing thermo-genetic selections on enzymes and proteins of industrial importance beyond the limitations of any other currently available system.

Using the $kan^{r2}$ allele, the Examples of the instant specification demonstrate how changing the host-vector environment from a moderate thermophile to an extreme thermophile can be used to allow for further thermo-genetic selections. Using the leuB insertion site, the methods of the instant invention were able to produce an additional 25° C. of temperature-shifting potential for further thermo-genetic selections on the $kan^{r2}$ allele.

Thus the instant specification teaches the recognition of the importance of the choice of host-vector in determining thermo-genetic potential of a system. Using slpA as the insertion site, for example, $kan^{r2}$ can be selected at 70° C.; using leuB as the insertion site, however, the same allele was selectable only up to 55° C. Since the power of thermogenetics is in large part determined by the potential for temperature-upshifts, the leuB environment of the instant invention provides a much greater range (about 55° C.–85° C. as opposed to about 70° C.–85° C.).

The disadvantage of a presumably lower expression system like leuB is seen when a mesophilic gene is used, such as kan. We observed, for example, that the wild-type kan could not be used as selectable marker in leuB even at the relatively low selection temperature of 45° C. The methods of the instant invention teach that in order to overcome the limitations of either a single high-expressing system or a single low-expressing system, that they both be used at the appropriate points in the process of making thermostable proteins. Ultimately, the most convenient and useful thermogenetic system is one that allows for regulated expression of the gene of interest. A simple change of conditions (for example, in nutrient supplementation) could be used to raise or lower expression levels and allow for a sophisticated control over the appropriate selection temperature for thermo-stabilizing mutations.

The *T. flavus*-leuB system of the instant invention is useful for the further thermo-stabilization of $kan^{r2}$. It is superior to the other chromosome-integration system using a slpA gene because mutations in leuB are not harmful to the host as are slpA mutations, and because of the wider range available for thermo-genetic selections presumably because of the lower expression level of the leuB gene. The instant methods and compositions demonstrated in the instant disclosure are useful and convenient because plasmid constructions can be made in *E. coli*, and gene replacements can be constructed efficiently in Thermus, and the leuB region offers the possibility for regulated control over the expression level of the cloned gene of interest for thermogenetic selections. The constructs of the instant invention are useful as vectors for inserting and expressing exogenous genes in an extreme thermophile.

Other thermostability approaches have used plasmid-based systems without chromosomal integration. This is because plasmids are generally thought of as being stable, easy to work with, easy to handle, easily transferred from one strain to another, and easy to make large amounts of DNA from. Unfortunately, in Thermus, plasmid based systems which have been tried have yielded inconsistent results. Thermus plasmids are unstable, tend to form multimers. Most researchers who have tried Thermus have reverted back to Bacillus for dependability of working with the plasmids, although they have lost the advantages of the higher temperature range. A major advantage of the Thermus organisms over Bacillus is that a range of Thermus organisms exist with different optimal growth temperatures, and that proteins native to Thermus appear more stable outside the cytoplasm. The stability in Thermus appears to lie in the proteins themselves, whereas in Bacillus there appears to be a cytoplasmic factor involved. Thus the instant invention provides for an effective means of using Thermus by teaching methods for stable targeted chromosomal integration for protein expression under specific regulation.

In fact, in the only other reports of inserting exogenous genes into Thermus have been directed not at stable gene transfer, but at insertional mutagenesis techniques for inactivating specific genes, or in trying to utilize a transposon in

*Thermus aquaticus. Thermus aquaticus*, however has a lower temperature range and is not easily tranformed by exogenous DNA. Lasa et al inserted the kan$^{r2}$ gene a highly expressed region of the chromosome to attempt disruption. Unfortunately this cause a debilitating phenotype making it a bad general integration system.

Very few workers have realized the significant advantages of *T. flavus*. *T. flavus* is closely related to *T. thermophilus* but, in our hands, has a transformation efficiently nearly 10× that of *T. thermophilus*. In fact, it was surprising to find that over 1% of all DNA molecules incubated with competent *T. flavus* cells are recombined into the chromosome of *T. flavus* in a transformation. This is important for transforming a series of mutagenized DNA molecules into the chromosome to increase the number of mutants which can be screened. Our system also has a lower expression level which is regulated by the leucine biosynthetic operon of *T. flavus*. This is very important for adjusting expression levels prior to the instant invention all workers in the field have focus on high protein expression at high temperatures in the belief that this was the most effective way to measure and select for mutations cenferring thermostability.

Our system also incorporates the use of kan$^{r2}$ at 55° C. instead of 65° C. which allows us to have a broader temperature range for selection of thermostabilizing mutations. The instant invention allows us to generate thermostable mutations in a stepwise fashion. For example, by starting the mutation process at 55° C. instead of 65° C., we have a larger range of temperatures in which mutations can occur before we reach the upper growth limit of the organism.

The advantages of regulation and control over expression and expression levels are that the perceived thermosability of an enzyme is related to its expression level as well as the temperature.

In an effort to increase the thermostability of a protein, the selectable or screenable level of thermostability is observed as a function of how much protein is present at a given temperature. The measurable thermostability in a genetic selection or screen is dependant on both the half-life of the protein and the expression levels of the gene. In an overexpressing system, the temperature range available to increase thermostability is reduced since more total activity is present at any given time. While the In a low expression system, there is much less protein at any given temperature giving a wider range of temperatures available. Thus the instant invention provides for a more efficient and flexible selection of thermostable proteins over a wider range of temperatures.

The level of expression of the gene of interest is very important for the practical application of a thermostabilization process. For proteins which are less stable to begin with, a higher expression level is initially desired. Once thermostabilizing mutations have been generated to allow the protein to function near the upper growth limit of the host organism, a lower expression level is desired. This will effectively reduce the amount of protein in the cell and therefore reduce the temperature which the protein is effective at. The process can once again be repeated to the upper growth level of the organism.

Further, by allowing for regulation, lethal mutations can be controlled and growth of the organism continued under non-lethal conditions.

The methods and compositions of the instant specification also provide for the pyrE nucleic acid sequence from *Thermus flavus* which is useful as a selectable target stable chromosomal integration into Thermus. Thus the instant invention provides for the stable integration into the chromosome of Thermus at two sites with the same or different proteins.

Thus the instant invention provides methods and compositions which will allow for the insertion and expression of a exogenous protein under specific regulation in Thermus where such protein can be subjected to further methods of the instant invention to generate more thermostable mutations.

The Examples described below are only intended by way of illustration, of the embodiments of the instant invention, and are in no way limiting as to the scope of the instant invention. One with ordinary skill in the art would be able to use the teachings of the instant specification to formulate and practice modifications and substitutions which are well within the scope of the instant disclosure.

EXAMPLE 1

Propagation of bacteria

Strains and Plasmids. *Thermus flavus* (*T. flavus*) AT62 is available from the American Type Culture Collection, #33923 (Saiki, et al, 1972, *Agric. Biol. Chem.* 36, 2357–2366). *Thermus thermophilus* (*T. thermophilus*) HB8 is available from the American Type Culture Collection, #27634, (Oshima, 1974, *International Journal of Systematic Bacteriology* 24:102–112). *Thermus aquaticus* (*T. aquaticus*) YT1 is available from the American Type Culture Collection, #25104, (Brock & Freeze, 1969, *J Bacteriol* 98:289–297). *E. coli* KC8 F$^-$ hsdR$^{31}$ X1488, leuB6, D(lac) X74, galE15, galK16, trpC9830, pyrF74::Tn5(Km$^R$), hisB463, rpsL(Str$^r$) was obtained from K. Struhl, Harvard University. *E. coli* MC1061 (Casadaban, et al., 1980, *J Bacteriol* 143:971–980) F$^-$ araD139 D(ara-leu)7696 galE15 galK16 D(lac)X74 rpsL (Str$^r$) hsdR2 ($r_K^-m_K^+$) mcrA mcrB1; and *E. coli* MC1066 (Casadaban, et al., 1983, *Recombinant DNA. Methods in Enzymology* 293–308) F$^-$ hsdR$^-$X1488, leuB6, D(lac)X74, galE15, galK16, relA1, spoT1, trpC9830, pyrF74::Tn5(Km$^r$), rpsL150($^r$) are in the ThermoGen strain collection. *E. coli* BW322, Hfr (PO45 of Hfr KL 16, serA (63'), lysA (61')), λ$^-$, relA, rfa-210::Tn10,pyrE70, spoT1, thi-1, was obtained from B. Bachmann (*E. coli* Genetic Stock Center), *E. coli* DH5a, F$^-$f80dlacZDM15 Δ(lacZYA-argF)U169 endA1 recA1 hsdR17($r_k^-m_k^+$) deoR thi-1 supE44 λ$^-$ gyrA96 relA1 was obtained from (Gibco/BRL Life Technologies). Plasmid pUB110 was obtained from N. Welker, Northwestern University; (Bacillus Genetic Stock Center, Ohio State University, Columbus, Ohio). Plasmid pUC-TK101 carrying the doubly thermo-stabilized kan gene (Y80/K130 (Liao, 1986; Matsumura, 1986) was obtained from H. Liao, University of Wisconsin. *E. coli* plasmids used included pUC19 (Sambrook, et al., 1989), pBluescript$_{II}$-SK(+) (Stratagene), and the Lorist 6 cosmid vector (Gibson, et al., 1987., *Gene* 53:275–281).

General growth media and conditions. Complex broth medium for growth of all Thermus strains was described in the American Type Culture Collection catalog as Medium 697, Thermus medium (TT); TT agar medium additionally contained 15 g/L Bacto-Agar (Difco). Transformation media (TM) for *T. flavus* was described by Koyama et al. (Koyama, et al., 1986, *J Bacteriol* 166:338–340). The minimal agar medium (Tmin) previously described by Yeh and Trela (Yeh and Trela, 1976, *J Biol Chem* 251:3134–3139) was used with the addition of 0.1% Casaminoacids (unless otherwise noted) for the phenotypic analysis of *T. flavus* auxotrophs. The composition of Tmin is as follows: sodium glutamate, 3 g; Thermus basal salts (5000×), 0.2 ml; after autoclave sterilization, 0.1% biotin, 100 ml; 1% thiamin, 10 ml; and 0.1% nicotinic acid, 50 ml, were added. Thermus basal salts (5000×) were prepared as follows: nitrilotracetic acid, 0.5 g; $CaSO_4.2H_2O$, 0.3 g; $MgSO_4.7H_2O$, 0.5 g; NaCl, 0.04 g; $KNO_3$, 0.515 g; $NaNO_3$, 3.45 g; $Na_2HPO_4$, 0.55 g; $FeCl_3$, 0.014 g; $MnSO_4.H_2O$, 0.11 g; $ZnSO_4 7H_2O$, 0.025 g; $H_3BO_3$ 0.025 g; $CuSO_4$, 0.008 g; $Na_2MoO_4.2H_2O$, 0.00125; $CoCl_2.6H_2O$, 0.0023 g; EDTA, 0.769 g; dissolved in distilled water, 1 liter. Standard growth conditions for *T. flavus* broth cultures were shaking at 280 rpm, one-inch circular displacement and 65° C. Agar cultures were incubated under water-saturated atmospheric conditions also at 65° C. unless otherwise stated. M9 minimal media, M63 minimal media, YT, and LB media (Sambrook, et al., 1989) supplemented with appropriate nutrients and antibiotics were used for general growth of *E. coli* strains.

EXAMPLE 2
Isolation of Ura⁻ Thermus and 5FOA selection

Construction of Ura⁻ mutants of Thermus. Mutants in the uracil biosynthetic pathway (Ura⁻) are extremely useful for genetic studies and genetic manipulation of bacterial and fungal organisms since a positive selection exists for either the loss or the presence of gene function. In yeast and *E. coli*, resistance to 5-Fluoro-orotic acid (5FOA) can be used as a positive selection (Boecke, et al, 1984. Mol. Gen Genet. 197:345–346) for mutants in several genes including two in the uracil biosynthesis pathway:URA1 and pyrE (coding for orotate phosphoribosyl transferase, OPRT) and URA3 and pyrF (coding for orotidine-5'-phosphate decarboxylase). By plating onto minimal media lacking uracil, only organisms which have wild-type pyr genes will be able to grow, allowing for a positive selection for non-mutant strains.

In order to obtain Ura⁻ strains of Thermus, mutagenesis of several Thermus strains including *T. thermophilus*, *T. aquaticus*, and *T. flavus* was performed by one of two methods. In the first method, we plated for uv-induced mutations by irradiating cells with 305 nm ultraviolet light for periods of time between two seconds and two minutes. Cells were plated onto TT media and exposed face-down, without the lid, on a uv transilluminator. An optimal mutagenesis by uv treatment was determined by selecting time points which killed between 20% and 50% of the cells. For all strains, this was approximately 20 seconds. Plates were allowed to grow for one to two days. Two ml of TT broth was added to the plates, mixed with the cells, and the mixture was scooped up for re-plating.

Optimal concentration of 5FOA (obtained from Sigma Chemicals) was determined by plating overnight cultures of the various wild-type Thermus strains onto a series of dilutions of 5FOA ranging from 20 µg/ml to 1 mg/ml and observing the minimal concentration of 5FOA needed to reduce background growth of bacteria on the media. The selection was found to work well with concentrations of 5FOA above 300 µg/ml for *T. aquaticus* and *T. thermophilus*, and above 500 µg/ml for *Thermus flavus*. Once mutants were generated they could be streaked out on media containing lower concentrations of 5FOA (150–300 µg/ml) since 5FOA was very expensive.

The pooled mutant mixtures plated onto TT media containing the appropriate concentration of 5FOA. Colonies which arose on the media were restreaked onto TT media containing 5FOA. Mutants could also similarly be generated by plating directly onto 5FOA selective concentrations and performing uv mutagenesis on these plates.

A second method which was developed and used to select for spontaneously generated 5FOA resistant mutants. The method consisted of plating the Thermus strains onto TT media, punching a hole in the center of the plate made aseptically with the back-end of a sterilized pasteur pipette, adding 500 µl of a 1 mg/ml solution of 5FOA to the hole allowing the 5FOA to diffuse out, and incubating at 65° C. Mutants resistant to 5FOA appeared after two days and were selected from the edges of a ring of killing created by the diffusing 5FOA. Mutants were purified by restreaking onto media containing 150–300 µg/ml of 5FOA.

Confirming Ura mutations. To verify that the mutants obtained were in the uracil biosynthetic pathway, the mutant colonies were patched onto Tmin media supplemented with uracil (50 µg/ml), onto Tmin without uracil, and onto TT media containing 150–300 µg/ml of 5FOA. The mutants which grew on Tmin supplemented with uracil and on TT with 5FOA but not on Tmin without uracil were identified and further characterized.

Reversion testing. The reversion frequencies of the mutations were analyzed by growing overnight cultures of the mutants and plating dilutions onto either TT rich media or Tmin without uracil added. The reversion frequencies of the mutations were calculated by dividing the total number of colony forming units per ml obtained on minimal media with the total number of colony forming units per ml on rich media. For most of the colonies, the reversion averaged about $5 \times 10^{-6}$ to $5 \times 10^{-7}$ which is consistent with a standard bacterial spontaneous mutation frequency. One in particular, TGF35, was used for the experiments described here which had a reversion frequency of about $1 \times 10^{-7}$.

EXAMPLE 3
Cloning of pyrE

Isolation of Thermus DNA. Genomic DNA of *T. flavus* was prepared by treatment of overnight Thermus cultures with 2% SDS in 50 mM Glucose, 25 mM Tris.HCl, pH 8 and 30 mM EDTA at 42° C. for 5 minutes and another 10 minutes in the presence of Proteinase K (20 mg/ml), followed by a 1 h Phenol/Chloroform/Isoamylalcohol extraction (25:25:1) and precipitation with 1.5 volumes of 100% ethanol. Mini-scale DNA preparations for library screening were carried out in 96-well microtiter plates. Large-scale and small-scale DNA preparations were performed using standard procedures described in (Sambrook, et al., 1989).

Construction of gene library. A λ-ori cosmid, Lorist 6 was used as vector and the *E. coli* strain DH5α as host for the construction of the gene library. The cloning of size-fractionated, Sau3A-digested DNA of *T. flavus* was achieved using HindIII-BamHI and EcoRV-BamHI "arms" of the cosmid (Sambrook, et al., 1989). Size fractionation was performed by ultracentrifugation through 10–40% sucrose gradients and fractions were analyzed by conventional electrophoresis. Fractions with average fragment sizes of 35–45 kb were used for cloning. Purified insert (300 ng DNA) was dephosphorylated to avoid cloning of non-neighboring DNA fragments, and ligated with an equimolar amount of cosmid arms in 10 ml of ligation mixtures and packaged in vitro into l heads. After infection of *E. coli* DH5α and plating on LB medium containing 30 µg/ml of kanamycin, a total of 700 cosmid clones were recovered. Individual colonies were picked and grown in 96-well microtiter plates and stored in 40% glycerol at −70° C.

Screening for Ura⁻containing region by transformation into Thermus. Since thermophile genes do not always complement *E. coli* mutations, because of either low expression or low activity in *E. coli* at 37° C., we decided to screen the *T. flavus* gene library in TGF35, a low-reversion Ura⁻ strain of *Thermus flavus* obtained by screening on 5-fluoro-orotic acid (5FOA). Individual recombinant gene library clones were grown in 96-well microtiter plates and mini-scale cosmid DNA preparations were performed. This DNA was transferred onto a lawn of competent *T. flavus* TGF35 cells on a Tmin media lacking uracil by spotting approximately 2 µl of DNA using a 48-prong replica tool (corresponding to ½ of a microtiter plate). A total of 672 recombinant cosmids were screened for their ability to transform the TGF35 to prototrophy. Cosmids containing a non-mutant sequence which covered a homologous region to the ura⁻ mutation in TGF35 were able to recombine into the Thermus chromosome by homologous recombination, replacing the mutant phenotype with a wild-type one and allowing growth on the minimal media. Positive results scored as growth on the minimal media and were seen with 28 cosmids. Cosmid 2A6 was chosen for further characterization.

Subcloning of the pyrE gene. Since TGF35 was an uncharacterized TF ura⁻ mutant we tested the cosmid clones for the ability to complement both *E. coli* pyrE (BW322) and pyrF (MC1066) mutants. Cosmid 2A6 was partially digested with Sau3A, dephosphorylated to avoid ligation of non-neighboring pieces and subcloned into the BamHI site of pUC19. The ligation mixture was used to test transformation of *E. coli* BW322 (pyrE) and MC1066 (pyrF) to prototrophy. Only BW322 was able to be transformed by selection on minimal media lacking uracil indicating that the clones were pyrE clones. Small-scale plasmid DNA preparations from 40 individually picked clones revealed the minimal insert size of 4 kb in plasmid pVUF10. A physical map of pVUF10.5 is shown in FIG. 1. The smallest Thermus DNA piece able to complement the *E. coli* mutant was found to be the 900 bp insert of pVUF10.5.9.

Determination and analysis of the nucleotide sequence of the pyrE gene. The 1.7 kb KpnI fragment of subclone pVUF10.5 was cloned in different orientations into pBL2-SK(+) and designated as pTG-F or pTG-R. Undirectional deletions were generated from pTG-F and pTG-R using Exonuclease III and S1 nuclease. We have sequenced the DNA clone with $^{35}$S corresponding to the KpnI fragment using the dideoxy sequencing method of Sanger. The sequence presented in FIG. 2 contains one major open reading frame (ORF) starting with ATG (position 262) and ending with TAG (position 810). The open reading frame shows homology with other genes encoding OPRT including *E. coli* and *Bacillus subtilis*.

EXAMPLE 4
Cloning of leuB

Cloning of leuB from *T. flavus*. Plasmid pTG100 (FIG. 3A), carrying the *T. flavus* leuB gene, was isolated by complementation of the leuB6 mutation in *E. coli* KC8. It was selected from a library of plasmids created through the ligation of *T. flavus* DNA, partially digested with Sau3A, to the BamHI site of the vector pTZ18R (Pharmacia P-L Biochemicals Inc., Milwaukee, Wis.).

Figure 3A:
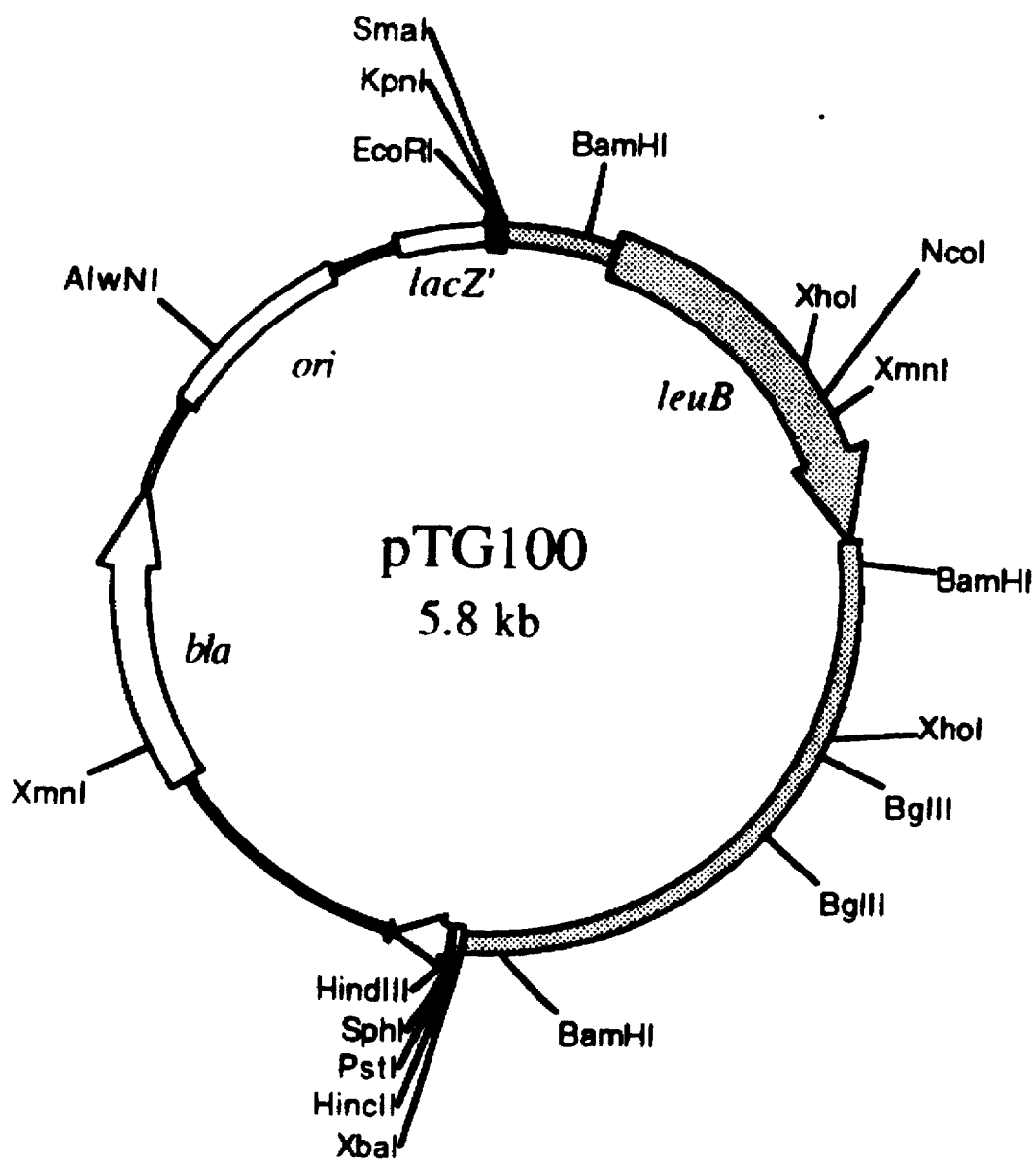
FIGS. 3A–3B are plasmid maps. (A) pTG100, derived from the *E. coli* vector pTZ18R digested with BamHI (open arrows and bars) and containing a 3 kb Sau3AI fragment of *T. flavus* chromosomal DNA encoding the leuB gene (shaded arrow) and flanking sequences (shaded bars). (B) Map of pTG100kan$^{r2}$, a plasmid derived from pTG100, contains the kan$^{r2}$ gene (solid dark arrow) inserted into the blunted NcoI site of the leuB gene (shaded arrow). The plasmid pTG100kan, described in the text, is identical to pTG100kan$^{r2}$ except it contains the wild-type allele of the kanamycin-resistance gene, kan, inserted into the blunted NcoI site of pTG100.

Plasmid pTZ18R (Pharmacia P-L Biochemicals Inc., Milwaukee, Wis.) linearized with BamHI was mixed under ligation conditions with 2–3 kb Sau3A fragments of *T. flavus* total DNA. The ligation products were added to competent *E. coli* KC8 cells, and the cells were plated on M9 minimal medium (Sambrook, et al., 1989) containing histidine (50 µg/ml) and tryptophan (50 µg/ml), uracil (10 µg/ml), ampicillin (100 µg/ml), and lacking leucine for the selection of Leu⁺ transformants. The Leu⁺ clones were analyzed and the plasmid with the smallest insert was designated pTG100 (FIG. 3A).

The 3 kb clone in pTG100 is analogous in its restriction map to the leuB genes from *T. thermophilus* (Nagahari, et al., 1980, *Gene* 10:137–145; Tanaka, et al., 1981, *J Biochem* 89:677–682; Croft, et al., 1987, *Mol Gen Genet* 210:490–497) and *T. aquaticus* (Kirino and Oshima, 1991, *J Biochem* 109:852–857) which encode the enzyme 3-isopropylmalate dehydrogenase (FIG. 2). This probably reflects a high degree of sequence homology between the three species since the leuB genes of *T. thermophilus* and *T. aquaticus* are already known have 87% homology in nucleotide sequence (Kirino, H. & Oshima, T., 1991, J. Biochem. 109, 852–857). The orientation and location for *T. flavus* leuB within pTG100 is based on this comparative analysis, specifically because the sites for BamHI, XhoI, NcoI, MscI, and XmnI all appear in the same order and relative spacing as the *T. thermophilus* sequence. This map indicates that the insert in pTG100 contains the entire leuB open reading frame, approximately 200 bp of upstream sequences, and 1.5 kb of downstream sequences. The smallest fragment containing the entire proposed leuB gene is the 1.1 kb BamHI fragment (FIG. 4); which was subcloned into the BamHI site of pUC19 and found to complement leuB6 in *E. coli* MC1066.

EXAMPLE 5
Inserting kan into leuB

Figure 3B:
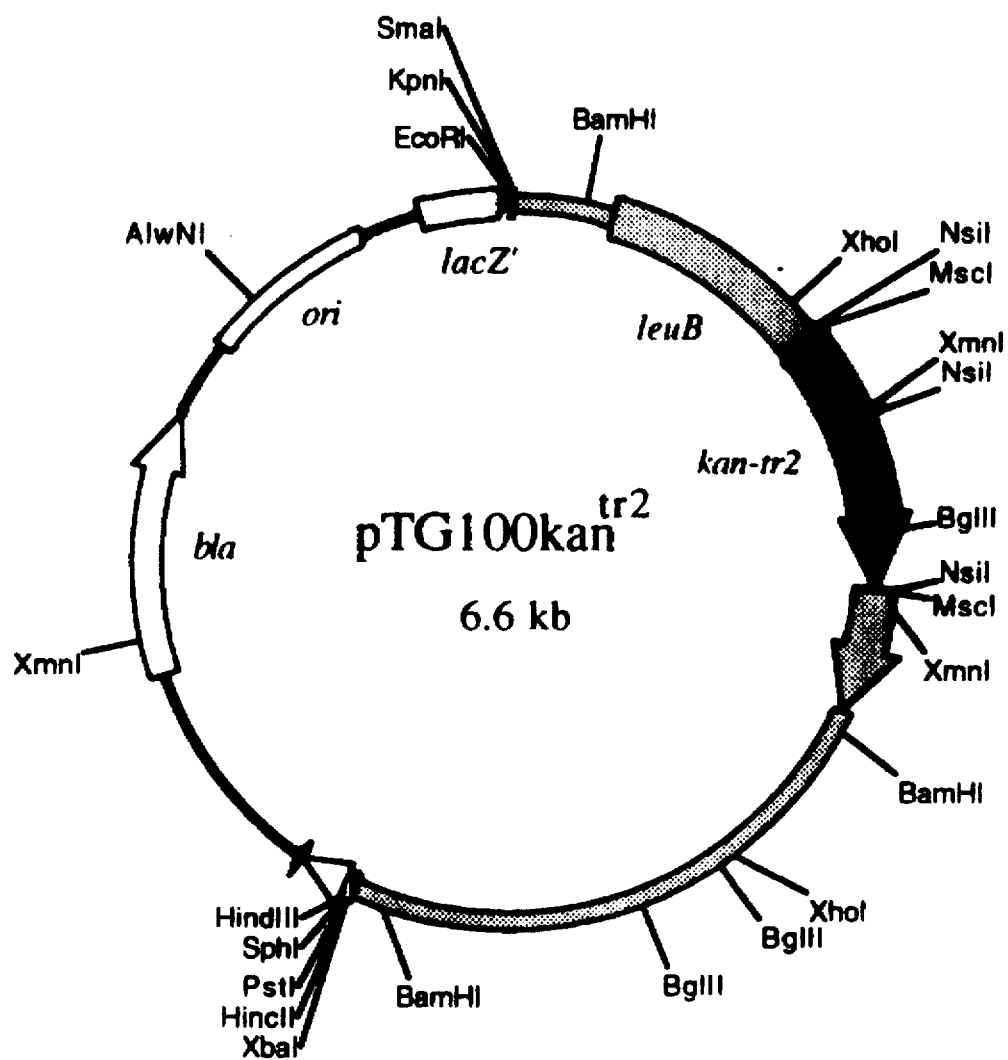

Insertion of kan and kan$^{tr2}$ into leuB. The kan gene from pUB110 (Lacey and Chopra, 1974, *J Med Microbiol* 7:285–297; Matsumura, et al., 1984, *J Bacteriol* 160:413–420) and the kan$^{tr2}$ gene from pUCTK101 (provided by H. Liao) were inserted into the unique NcoI site of leuB in pTG100 to create pTG100kan and pTG100kan$^{tr2}$ (FIG. 3B), respectively.

Figure 5:
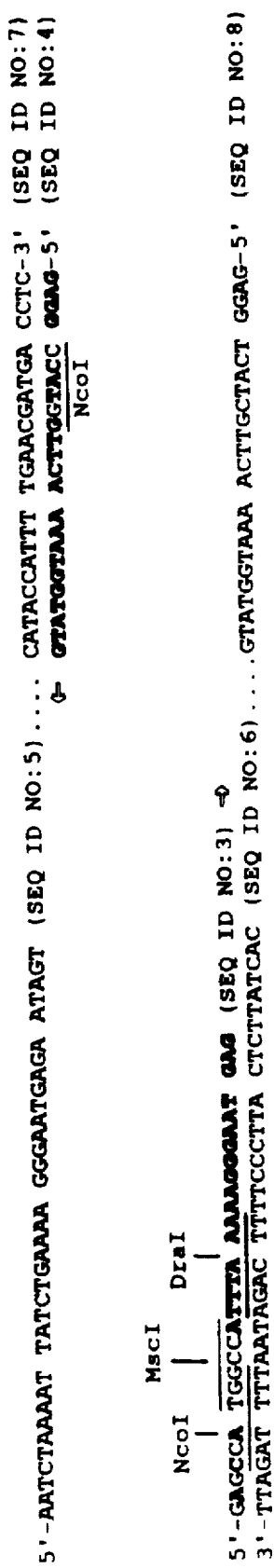
FIG. 5 shows PCR primer sequences for amplification of the kan and kan$^{r2}$ genes. Primer sequences are shown in bold type where they correctly pair with the template sequence. Top line, coding sequence for the kan gene; bottom line, anticoding strand of the kan gene. Arrows indicate direction of primer elongation. "PCR 3' primer (containing a NcoI site) is shown (SEQ ID NO: 4). PCR 5' primer (containing a NcoI MscI and DraI site), is shown (SEQ ID NO:3). Part of sense strand of the kan gene (SEQ ID NO: 5) and (SEQ ID NO: 7). Part of anti-sense strand of the kan gene (SEQ ID NO: 8) and (SEQ ID NO:6)."

The polymerase chain reaction was used to produce the two kan genes with NcoI sites at each end (FIG. 5). We used the PCR method described by Ponce and Micol with modifications, using buffer III and 30 cycles instead of their recommended 10 cycles to generate our PCR products (Ponce, M. R. & Micol, J. L., 1991, Nucl. Acids Res. 20, 623). Oligonucleotide primers were obtained from Operon Technologies, Inc. (Molene, Calif.).

Figure 4:
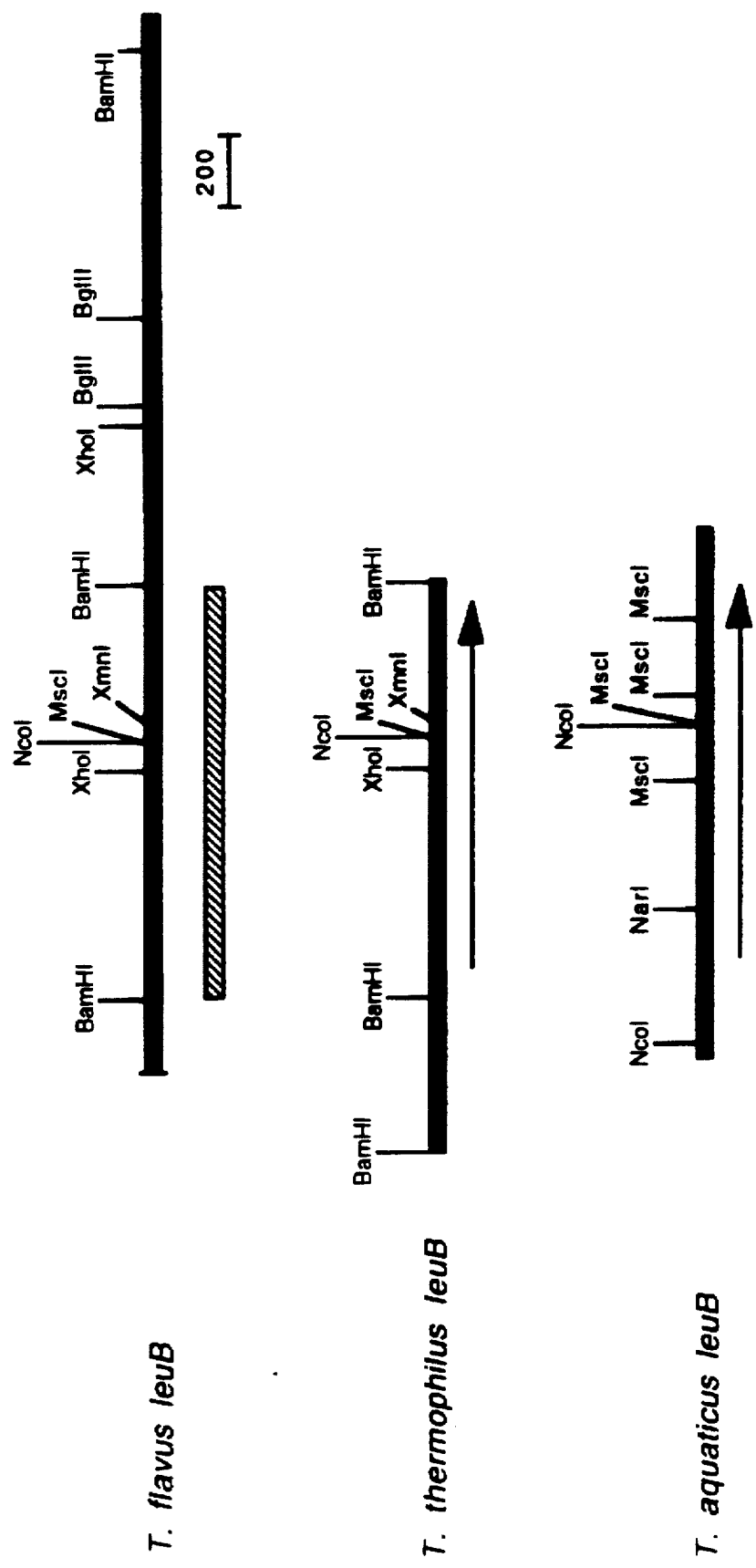
FIG. 4 is a comparative analysis of the restriction maps of leuB genes from three different Thermus species: *T. aquaticus* leuB (Kirino, H. & Oshima, T., 1991, *J. Biochem.* 109, 852–857) (bottom), *T. thermophilus* leuB (Croft, J. E., Love, D. R. & Bergquist, P. L., 1987, Mol. Gen. Genet. 210, 490–497) (middle) and *T. flavus* leuB (top, this study). The bar underneath the *T. flavus* restriction map is the smallest subclone of the DNA fragment that was able to complement the leuB mutation in *E. coli* KC8.

Circular pTG100 DNA was mixed with a PCR DNA in the original PCR reaction buffer containing TaqI polymerase. NcoI was added with the recommended reaction buffer from NEB, and the reaction was allowed to incubate at 37° C. After 3h NcoI was inactivated by heating to 65° C. for 20 min and allowed to cool slowly to room temperature, during which time the TaqI polymerase was able to fill-in the NcoI overhangs to create blunted ends on both the PCR DNA and pTG100 (FIG. 4). The DNA was ethanol precipitated and then resuspended in a solution suitable for ligation of the DNA in the reaction. The products of ligation were transformed into *E. coli* MC1061 and transformants were selected on YT agar plates ("Molecular Cloning," 2nd Ed. Sambrook, Fritsch and Maniatis eds. 1989 Cold Spring Harbor Laboratory Press) supplemented with 10 or 20 µg/ml of kanamycin and 100 µg/ml of ampicillin. Five transformants from each ligation were analyzed: 9 of which carried a single insert in the same orientation as the leuB gene in pTG100. The tenth transformant, a kan double clone, carried both inserts in the opposite orientation to leuB. The insertion of the kan gene into the NcoI site of pTG100 was confirmed by restriction analysis of the plasmids from transformants that were resistant to both Ap (100 µg/ml) and Km (10 µg/ml). Restriction analysis showed that the NcoI sites had been converted, as predicted, through the joining of blunt NcoI sites to produce NsiI sites at the junctions (FIG. 5).

Alternatively, the kan$^{tr2}$ gene could be cloned into the TthIIII site to disrupt the pyrE gene using the same methods as above.

EXAMPLE 6
Transformation of *T. flavus* and Confirming insertion of exogenous gene Testing for disruption of the leuB gene. To test for the Leu$^+$ complementation phenotype, pTG 100 plasmid DNA, plasmid DNA from one of the kan transformants (pTG100kan) and one of the kan$^{tr2}$ transformants (pTG100kan$^{tr2}$), was used to transform *E. coli* MC1066. As expected, only pTG100 plasmid DNA was able to complement the leuB6 mutation, indicating that the insertions of kan and kan$^{tr2}$ had inactivated leuB. Finally, we observed that the expected NcoI sites were not present at the ends of kan and kan$^{tr2}$ in their respective plasmids, but were replaced by NsiI sites. Apparently, the NcoI ends were filled-in to form blunt ends by Taq polymerase, which had not been removed from the reaction, and upon ligation with the similarly filled-in vector ends, created the NsiI sites. Three other clones which were isolated in a similar experiment which contained an Nco I site upstream (pTG100kan$^{tr2}$cs), downstream (pTG100kan$^{tr2}$sc), or at both ends (pTG100kan$^{tr2}$cc) of the kan$^{tr2}$ gene insertion with an NsiI site at the other position.

Disruption of chromosomal leuB by gene-replacement with kan$^{tr2}$ using pTG100kan$^{tr2}$. Both pTG100kan and pTG100kan$^{tr2}$ were used in transformation reactions with *T. flavus*. A transformation protocol for *T. flavus* AT62 (ATCC 33923) has been described (Koyama, et al., 1986, J. Bacteriol. 166:338–340). The procedure used in this study for the wild type strain was a slight modification of Koyama's. Individual colonies from TT plates were used to inoculate 2 ml test tube cultures of TM and grown overnight (17 h) at 65° C., 280 rpm. 1.6 ml of the test tube culture was used to inoculate 50 ml of TM broth in a 250 ml Ehrlenmeyer flask and the flask was incubated at 65° C., 280 rpm for 4 h. Transformations involved adding 1 µg of plasmid or 4 µg of chromosomal DNA to 500 µl portions of the 4 h culture; the cells and DNA were incubated at 65° C. while shaking, for 1 h. The cells and DNA were then diluted and plated on TT plates containing the appropriate supplements [kanamycin sulfate (Sigma Chemical) was used at 20 µg/ml final agar concentration] and incubated at 65° C. for 2–3 days until transformants arose. The growth temperature and incubation temperature for transformation plates was 65° C. instead of at 70° C. as described by Koyama (1986).

Selections for transformants were performed on agar containing 20 µg/ml of kanamycin. The initial selection temperature was chosen to be 65° C. as described in the original *B. stearothermophilus* system (Liao, 1986) and in later systems developed for Thermus (Mather and Fee, 1992, Appl Environ Microbiol 58:421–425; Lasa, et al., 1992, J Bacteriol 174:6424–6431; Lasa, et al., 1992, Molec Microbiol 6:1555–1564). Analysis of the colonies appearing at this temperature revealed that the majority (averaging 82%) of the pTG100kan$^{tr2}$ transformants were not stably kanamycin-resistant or Leu$^-$. The remainder of the pTG100kan$^{tr2}$ transformants were generally larger colonies which were Leu$^-$. These colonies restreaked at 65° C. on kanamycin media, although grew poorly. None of the transformants from the pTG100kan plasmid containing the non-thermostable kan gene were stably kanamycin-resistant or Leu$^-$. In summary, although the Leu$^-$ kanamycin resistant transformants could be isolated at 65° C., they were difficult to find among the more abundant background growth. The pTG100kan transformations produced no stable kanamycin-resistant or Leu$^-$ colonies.

We next performed Southern analyses on a sample of Leu$^+$ and Leu$^-$ colonies from the pTG100kan$^{tr2}$ transformations. Chromosomal DNA from the following: three pTG100kan$^{tr2}$ Leu$^-$ transformants, two Leu$^+$ colonies, and the parental wild-type strain, were subjected to Southern hybridization analysis (FIG. 6). *T. flavus* total DNA was prepared for Southern analysis as follows. Cells from 5 ml overnight TT broth cultures grown at 65° C. were pelleted and resuspended in 900 µl of 25 mM pH 8.0 Tris buffer containing 10.3% sucrose, 25 mM EDTA and 1 mg/ml lysozyme (Sigma). After a 30 min incubation at 37° C., 250 µl of 500 mM EDTA, 2.5 µl of Proteinase K (20 mg/ml, Sigma), and 140 µl of 10% aqueous lauryl sulfate (SDS) were mixed in. After a second 30 min incubation at 37° C., 150 µl of phenol/chloroform/isoamyl alcohol (25:24:1) was mixed-in until the solution appeared homogeneous. The solution was separated into two phases by a 5 min microcentrifugation and 4 µl of RNase (10 mg/ml) was gently mixed into to the upper, aqueous phase and the tube was incubated at 37° C. for another 30 min followed by vigorous mixing of the two phases and a second micro-centrifugation. The aqueous phase (0.9 ml) was transferred to a new tube to which 100 µl of 3M sodium acetate was added and 1 ml of isopropanol. The chromosomal DNA was allowed to precipitate into a globule which was transferred by pipet and washed in a tube containing 70% ethanol and then transferred and dissolved in 100 µl of TE, pH 8.0. Enzymatic digestions for Southern analyses were performed using between 2 and 8 µl of these DNA solutions. Southern analyses were performed using the materials and methods contained in the Genius nonradioactive DNA labeling and detection Kit, (Boehringer Mannheim, Indianapolis, Ind.).

Figure 6A:
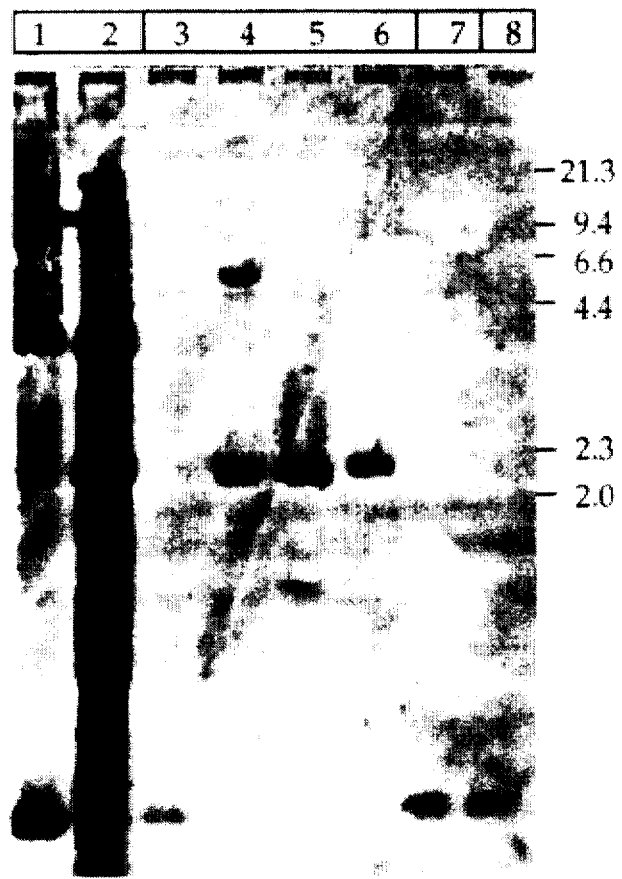
FIG. 6A–6B show Southern hybridization of *T. flavus* total DNA showing gene replacement of kan$^{r2}$ into the leuB region of the chromosome. (A) NcoI and BamHI-double-digested DNA (lanes 1–8); DNA from Kan$^R$ Leu$^-$ transformants, lanes 4–6. DNA from untransformed cells, lanes 3, 7, 8. DNA size markers (kb units) indicated to the right. (B) Schematic representation of DNA from pTG100kan$^{r2}$ transformants showing the insertion of the kan$^{r2}$ gene (black arrow) into the leuB gene (shaded arrow) of the *T. flavus* chromosome (shaded line). Striped bar indicates DNA fragment used as the probe in the hybridization reaction.
Figure 6B:
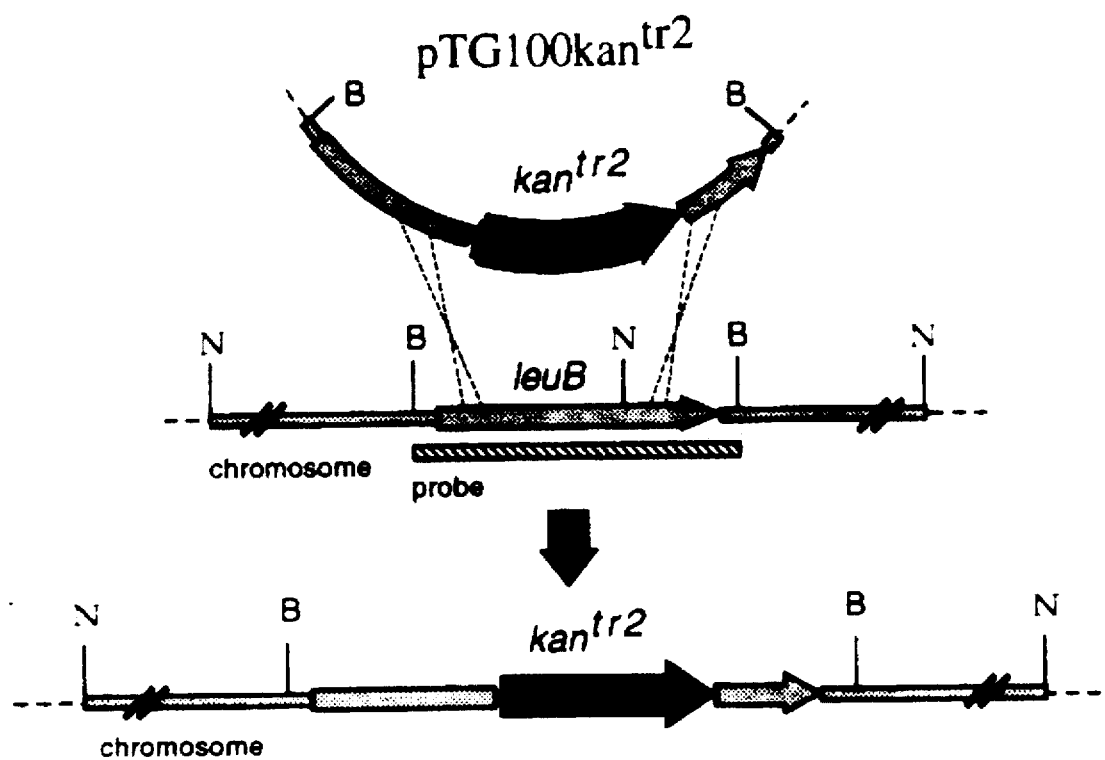

All three Leu$^-$ transformants were found to have acquired an insertion of the size expected for kan$^{tr2}$ in the leuB gene confirming that the kan$^{tr2}$ gene had been inserted into the leuB region of the chromosome, whereas none of the Leu$^+$ strains had inserts (lanes 4–6, FIG. 6A). The data, therefore, provide evidence for a double recombination gene-replacement event in which the kan$^{tr2}$ gene was inserted into leuB in the *T. flavus* chromosome.

EXAMPLE 7
Stable gene insertion

Stable Leu$^-$ Kan$^r$ phenotype in *T. flavus*. Primary transformants of *T. flavus* with pTG100kan$^{tr2}$, selected for growth on TM plates containing 20 µg/ml of Km, were transferred to unsupplemented Tmin agar plates and to Tmin agar plates supplemented with 50 µg/ml L-leucine. The Leu$^-$ phenotype was scored by careful observation of the two plates and by a comparison of growth to the wild-type strain, after 3–4 days incubation at 65° C.

The transformants carrying gene-replacements were found to be stably kanamycin-resistant and Leu$^-$ even after three passages on non-selective agar media. The kan$^{tr2}$ gene was not spontaneously amplified or deleted from the chromosome as shown by unchanged Southern banding patterns (not shown). Transformants with pTG100kan$^{tr2}$ appear to efficiently and completely insert kan$^{tr2}$ sometime during the growth of the primary transformants or while being subcultured to produce the DNA for Southern analysis. No evidence of single-crossover intermediates was obtained in the sample tested. This contrasts with other prokaryotic gene-replacement systems where it is common to isolate single-crossover intermediates in integration and replacement process. The difference presumably reflects a more rapid rate of recombination in the *T. flavus* system.

EXAMPLE 8
Optimizing temperature

Effect of temperature on pTG100kan$^{tr2}$ transformation efficiencies and background growth. During the course of an experiment to observe the effect of lowering the temperature from 65° C. to 55° C. for selection of pTG100kan$^{tr2}$ transformants we observed at least a 100-fold increase in the efficiency of transformation and the elimination of the spontaneous kanamycin resistance growth on the plates. No transformants were obtained with pTG100kan (containing the non-thermostable kan allele) even after extended incubation periods.

Further reduction of the initial selection temperature to 45° C. produced essentially the same results observed at 55° C. for both plasmids. The transformants with pTG100kan$^{tr2}$ grew at normal rates: two to three days to appear at 55° C., and up to two weeks to appear at 45° C. Again, no transformants appeared with pTG100kan. At 70° C. no transformants or background colonies appeared using either plasmid.

In summary, at 55° C., kanamycin-resistant transformants were reproducibly obtained and easily identified when transformed with a plasmid carrying the thermostabilized marker, kan$^{tr2}$, but not when transformed with the wild-type marker, kan. Also, transformation efficiencies were at least 100-fold higher at the lower temperatures tested and no background growth appeared.

EXAMPLE 9
Thermostable Mutant Selection

Temperature shifting—selection for more highly temperature-resistant mutants. Although transformants of *T. flavus* with pTG100kan$^{tr2}$ grew well in subculture at 55° C., they could not grow at 65° C. In order to see if mutations that would make the strain able to grow stably at higher temperatures could be selected in the kan$^{tr2}$ transformants, cells from the 55° C. kan$^{tr2}$ transformants were plated at high density on agar medium containing kanamycin and incubated at 65° C. Spontaneous mutants that survived the temperature shift appeared at a frequency of one in $10^{-6}$ and could be distinguished from the background growth by their larger size. Plasmid pTG100kan$^{tr2}$ transformants grew normally in subculture on kanamycin-supplemented agar at 65° C. and were designated as Kan$^{tr2+}$.

It will be possible to take *T. flavus* cells which contain kan$^{tr2}$ in the chromosome and treat with a mutagen to increase the mutation frequency. Alternatively, a more directed mutagenesis approach could be taken to increase the mutant frequency of kan$^{tr2}$ specifically. Plasmid DNA could be mutated in *E. coli* before tranformation into *T. flavus* by treating the cells with hydroxyulamine. In this approach, *E. coli* cells harboring pTG100kan$^{tr2}$ are subjected to hydroxylamine at a series of different concentrations. Hydroxylamine causes mutations preferentially on plasmid molecules in *E. coli* (Miller, 1972). Plasmids prepared from the mutagenized *E. coli* are then used to transform *T. flavus* and the Thermus cells are plated under conditions of the first temperature shift.

Another directed mutagenesis approach utilizes the error-prone PCR technique (Spee et al., 1993, Nucleic Acids Res. 21:777–8) In this approach, the kan$^{tr2}$ (or other gene of interest) is mutagenized prior to cloning into the gene replacement vector. The kan$^{tr2}$ gene is mutagenized by using the primers which were previously used to clone it into the NcoI site. Two PCR reactions are run, one with either dA or dG present in reduced amounts in the amplification mix. This increases the Taq DNA polymerase error rate and introduces mutations. Nucleotide analog dl is optionally added to increase the mutation frequency further. This mixture is then cloned as previously described into the NcoI site of pTG100 (or if a second gene is being introduced and mutagenized into pTG100kan$^{tr2}$ sc) and directly used to to transform *T flavus*, or can be used to transform *E. coli*, pooled, and then used to retransfrom Thermus.

Linkage of the Kan$^{tr2+}$ and Leu$^-$ phenotypes. In order to determine whether any of the mutations leading to the Kan$^{tr2+}$ phenotype were linked to leuB we retransformed the mutant DNA into wild-type *T. flavus*. This would reveal whether the mutations were likely to be located in or near to the kan$^{tr2}$ gene (linked), or far from the kan$^{tr2}$ gene (unlinked). Total DNA was isolated from the Kan$^{tr2+}$ Leu$^-$ mutants and used to transform wild-type *T. flavus* at 55° C. Primary transformants were selected at 55° C. and screened for kanamycin-resistance at 65° C. (i.e., the Kan$^{tr2+}$ phenotype) and for Leu$^-$. The results showed that in one out of ten of the mutants, the Kan$^{tr2+}$ phenotype was 100% linked to the Leu$^-$ phenotype in a sample of 50 transformants. The other nine out of ten transformants showed lower degrees of linkage suggesting that the mutation was further away from the kan$^{tr2}$ gene.

EXAMPLE 10
Multiple Gene Insertion

Insertion of multiple exogenous genes. The following describes an example of the instant invention which could be used to insert a second (or multiple) exogenous genes into the Thermus chromosome, utilizing the selectability of kan$^{tr2}$ to insert a gene which may not have a selection or which may not operate at the growth temperature of the Thermus strain used.

In this example, a recombinant molecule is made which contains the gene of interest cloned into either the upstream NcoI site of pTG100kan$^{tr2}$cs or the downstream NcoI site of pTG100kan$^{tr2}$sc or a polylinker which is inserted at one of these sites. One example of doing this is to use plasmid pTG100kan$^{tr2}$cs is digested with endonuclease NcoI, filled-in with the DNA polymerase Klenow fragment, and dephosporylated with Calf-intestinal alkaline phosphatase. The gene of interest is similarly made blunt-ended, only without phosphorylation, and ligated into the filled-in NcoI site. A recombinant molecule with the fragment in the desired orientation is used to transform *T. flavus* and selection for kanamycin resistance at 55° C. can be used as previously described for the kan$^{tr2}$ gene. If the gene of interest is placed upstream of kan$^{tr2}$, expression of kan$^{tr2}$ indicates that the gene of interest has likely been transcribed also. Once transformants have been obtained, selection on kanamycin media is no longer required since gene replacements are stable.

EXAMPLE 11
Monitoring Expression

Monitoring expression of gene replacement products. The following describes an example of the instant invention which could be used to monitor expression levels of genes inserted into the chromosome of Thermus. During a thermostabilization process, several types of mutants can be generated which allow selection of an increased level of activity at higher temperatures. If a gene, such as kan$^{tr2}$ is used, selection at higher temperatures could mean that the thermostability of the protein has increased, or could mean that the expression level of the gene has increased. Mutants need to be individually analyzed to determine if a thermostability mutation or some other mutation has been obtained.

In this example, a reporter gene which can be easily assayed, such as one with a β-galactosidase activity, is inserted downstream of the gene of interest can be used to screen away mutations which effect expression levels. One such gene is tbg, which has been cloned from *T. aquaticus* and which produces a thermostable broad specificity β-galactosidase enzyme, Tbg. Tbg catalyzes the hydrolysis of a wide range of glycolytic compounds including compounds which can be easily assayed such as 5-bromo-4-chloro-3-indolyl-galactopyranoside (X-Gal), and 5-bromo-4-chloro-3-indolyl-glucopyranoside (X-Glu) which form blue precipitates when hydrolyzed and o-nitrophenyl-β-D-galactopyranoside (ONPG) and o-nitrophenyl-β-D-glucopyranoside which can be quantitated spectrophotometrically.

Plasmid pTAQL2 is is used to PCR amplify a fragment containing tbg. The primers are designed to include the tbg ribosomal binding site and start codon and to have NcoI sites at each end after amplification. The PCR product is digested with NcoI and ligated into a filled-in NcoI site in pTG100kan$^{r2}$sc. Insertion into the chromosome of Thermus will allow the tbg gene to be placed under control of the leucine promoter so that levels of expression can be easily monitored using one of the assayable substrates described above according to Miller (Miller, 1972). By supplementing the agar media with X-gal or X-glu (approximately 2 ml of a 4% solution in n-n-dimethylformamide per liter of media), one can visualize expression levels on a plate by observing how blue the individual colonies are. The expression levels can be quantitated using a substrate such as ONPG and assayed according to Miller.

Derivatives of this plasmid can be made which contain a polylinker upstream of kan$^{r2}$ and the tbg inserted downstream to moniter expression levels. This system is used to optimize expression from the leucine promoter or to screen for mutants in a temperature shift experiment which have an increased activity of the desired gene but not of the downstream tbg.

EXAMPLE 12

Chromosomal Transfer

Transferring to other strains of Thermus

The methods and compositions of the instant disclosure allow for the possible use in the transferring altered chromosomes from one Thermus species to another.

In order to have a broader range of temperatures with which to thermostabilize potential exogenous proteins, transferring the gene replacement event to other strains of thermus could be readily accomplished by chromasomal transfer. (Koyama et al. 1986) Because of its high transformation frequency for exogenous DNA sequences, *Thermus flavus* is the best starting point for chromosomal insertion. Once accomplished in *flavus* the transformation frequency is relatively high with chromosomal transfers to other related thermus strains with different optimum temperatures for growth.

---

What we claim is:

1. A method of evolving thermostable proteins which comprises subjecting host cells to elevated temperatures for selection of mutated thermostable proteins in a step-wise fashion, where said host cells were produced by growing host cells and selecting for a stable host cell transformant, where the host cells have been transformed with a vector, where said vector transforms the host cell by inserting a targeting DNA sequence into a targeted chromosomal DNA sequence of a thermophilic microorganism, where said insertion results in a benign mutant phenotype, which targeting DNA sequence contains an exogenous DNA sequence which encodes an exogenous protein, which exogenous DNA sequence will recombine into the targeted DNA sequence, and the expression of said exogenous protein from said exogenous DNA sequence is regulated by the chromosome.

2. The method of claim 1 where the exogenous DNA sequence encodes a kan gene.

3. The method of claim 1 where the targeting DNA sequence and the targeted chromosomal DNA sequence is a leuB gene.

4. The method of claim 1 where the targeting DNA sequence and the targeted chromosomal DNA sequence is a pyrE gene.

5. A host cell which has been produced by the method of claim 1.

\* \* \* \* \*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1707 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 262..810

( x i ) SEQUENCE DESCRIPTION: SEQ ID NO:1:

```
GGTACCGGGA  GGGTCCCTGG  AGCCGGGTGG  GGATGGTGGT  GGGGGCCACC  TACCCGGGGG       60

CCGTGGCTCG  GGTGCGGGAA  AGGGCGCCCC  ACGCCCCCCT  CCTCCTCCCC  GGCGTGGGGG      120

CCCAGGGGGG  GAGGCCCTCA  AGGGGAGGG   GCTTCTTTTC  GCGGCGAGCC  GGGCCCTCTA      180

CTACCCTGGG  GGAAGGCCGG  ACCTAAAGGC  CGCCCTGGAG  GCGGCGGAGG  CCCTCTTGAA      240

GGCTCTGGTA  GAGTAGGGGG  G ATG GAC GTC CTG GAG CTT TAC CGG AGG ACG           291
              Met Asp Val Leu Glu Leu Tyr Arg Arg Thr
               1               5              10

GGG GCT CTT CTA GAG GGC CAC TTC CTC CTG CGC TCG GGG ATG CAC TCC             339
Gly Ala Leu Leu Glu Gly His Phe Leu Leu Arg Ser Gly Met His Ser
         15              20              25

CCC TTC TTT TTG CAG TCG GCG GCC CTC CTC CAG CAT CCC CTT TAC GCC             387
Pro Phe Phe Leu Gln Ser Ala Ala Leu Leu Gln His Pro Leu Tyr Ala
         30              35              40

GAG GCC GTG GGG GAG GCT TTG GGA AAG CTC TTT GAG GAC GAG AAG GTG             435
```

```
Glu Ala Val Gly Glu Ala Leu Gly Lys Leu Phe Glu Asp Glu Lys Val
         45                  50                  55

GAC TTC GTC ATC GCC CCG GCC ATC GGG GGC GTG GTC CTT TCC TTC GTG      483
Asp Phe Val Ile Ala Pro Ala Ile Gly Gly Val Val Leu Ser Phe Val
         60                  65                  70

GTG GCG AAG GCC TCG GGC CCG GGC CCT CTT CGC CGA GAA GGA CGG AAG      531
Val Ala Lys Ala Ser Gly Pro Gly Pro Leu Arg Arg Glu Gly Arg Lys
 75                  80                  85                  90

GGG AGG GAT GCT CAT CCG CAA GGG GCT CAC CGT GAA CCC GGG CGA CGC      579
Gly Arg Asp Ala His Pro Gln Gly Ala His Arg Glu Pro Gly Arg Arg
                 95                 100                 105

TTC TTG GCG GTG GAG GAC GTG GTA ACC ACC GGG GAG AGC GTC CGC AAG      627
Phe Leu Ala Val Glu Asp Val Val Thr Thr Gly Glu Ser Val Arg Lys
             110                 115                 120

GCG ATC CGG GCG GCG GAG GCC CGG GGC GGG GTT TTG GTG GGC GTG GGG      675
Ala Ile Arg Ala Ala Glu Ala Arg Gly Gly Val Leu Val Gly Val Gly
         125                 130                 135

GCC ATC GTG GAC CGG AGC GGG GGC AGG GCG GCC TTC GGC GTG CCC TTC      723
Ala Ile Val Asp Arg Ser Gly Gly Arg Ala Ala Phe Gly Val Pro Phe
     140                 145                 150

CGC GCC CTC CTC GCC TTG GAG GTT CCC CAG TAT CCC GAG GAG GCC TGC      771
Arg Ala Leu Leu Ala Leu Glu Val Pro Gln Tyr Pro Glu Glu Ala Cys
155                 160                 165                 170

CCC CTC TGC CGG GAG GGG GTG CCC TTG GAG GAG GTT TAGGGTGCGC           817
Pro Leu Cys Arg Glu Gly Val Pro Leu Glu Glu Val
                175                 180

TTCCTCGCTG CCCTTCTTCT CGGCCTTTTC TCCCTGGCCC TCGCGGCCCC GGAGGAGGCC    877

GCGAGGGAGA CCGTCGCCCG GTGGCTCAGG GGGGAGCTCT CCCCGAGCCT CGAGGAGGTC    937

CTTAGGGCCC CTCCGGAGGA GGCCCCGAGG CTCCTCGAGC GTTCGCCCTC TTCCCCCCGC    997

CCCCCGATGG GCTTACCGTC AACCTGGAAA GCCCCGAGGT GGAGGGGAAC CGGGTCTCCT   1057

TCCCGGCCGC CCTCGGGGAG GAGGTGGGGG AGGTGGTGGT GGTCCTGGAA GGGGGGGAGG   1117

CCAGGCGGGT CTACTTCCGC CCCGAGGCTC GGGTGCCCGC CTACCTCCTC ACGCCCCTCG   1177

CGGGCTTTGG GTTTTTCCTC CTCTCCCTCT TTGGGTCTT CCTCCTCCTC AGGCCCTCCC    1237

CCTTCCGGGC CTGGCTTCTT GAGGCCTGGG CCTTGGTCCG GTCCAGAGG GGCCTTTACC    1297

TCTTCACCAA CCTCTTCCTC TACGGCCTAT CGCCCTGGG GAGCCTTCTC GCCTACGCCA    1357

TGCCCGAGCT CGCCCGGGCG GTGCAGGTCC TCTTCGGGGG CGCCTTGGAG GCCATCGGCC   1417

TCCAGGAGGC GGTGGGGAAG GGCGTTTTGG TCCTCGCTGG GGTCATCTTT CACTGGAATT   1477

TCAGCCAGGG GCTTTTCCTC ACAGGGCTCC TTCCCGCCTT GCTCTTGGGG GTTCCTGTGC   1537

TCCTCCTCAA CGCCCTCCGC TACTTCGCTT CGTTCGCCCT CTCCCCGGCC CTTCTGGGAA   1597

GCGCCTTCCT CTTCCACCTG CCCACCCTTC TTTTGGAGCT TCAGGCCTAC ATCCTCGTCA   1657

CTTCGGCGGG CTCGTCCTCC TCGCCCGGGT GGCCGGGGGG CAGGGGTACC              1707

( 2 ) INFORMATION FOR SEQ ID NO:2:

( i ) SEQUENCE CHARACTERISTICS:
            ( A ) LENGTH: 182 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

Met Asp Val Leu Glu Leu Tyr Arg Arg Thr Gly Ala Leu Leu Glu Gly
 1               5                  10                  15
```

|     |     |     |     |     |     |     |     |     |     |     |     |     |     |     |     |
|-----|-----|-----|-----|-----|-----|-----|-----|-----|-----|-----|-----|-----|-----|-----|-----|
| His | Phe | Leu | Leu | Arg | Ser | Gly | Met | His | Ser | Pro | Phe | Phe | Leu | Gln | Ser |
|     |     |     | 20  |     |     |     |     | 25  |     |     |     |     | 30  |     |     |
| Ala | Ala | Leu | Leu | Gln | His | Pro | Leu | Tyr | Ala | Glu | Ala | Val | Gly | Glu | Ala |
|     |     |     | 35  |     |     |     | 40  |     |     |     |     | 45  |     |     |     |
| Leu | Gly | Lys | Leu | Phe | Glu | Asp | Glu | Lys | Val | Asp | Phe | Val | Ile | Ala | Pro |
|     |     | 50  |     |     |     | 55  |     |     |     |     | 60  |     |     |     |     |
| Ala | Ile | Gly | Gly | Val | Val | Leu | Ser | Phe | Val | Val | Ala | Lys | Ala | Ser | Gly |
| 65  |     |     |     |     | 70  |     |     |     |     | 75  |     |     |     |     | 80  |
| Pro | Gly | Pro | Leu | Arg | Arg | Glu | Gly | Arg | Lys | Gly | Arg | Asp | Ala | His | Pro |
|     |     |     |     | 85  |     |     |     |     | 90  |     |     |     |     | 95  |     |
| Gln | Gly | Ala | His | Arg | Glu | Pro | Gly | Arg | Arg | Phe | Leu | Ala | Val | Glu | Asp |
|     |     |     | 100 |     |     |     |     | 105 |     |     |     |     | 110 |     |     |
| Val | Val | Thr | Thr | Gly | Glu | Ser | Val | Arg | Lys | Ala | Ile | Arg | Ala | Ala | Glu |
|     |     |     | 115 |     |     |     | 120 |     |     |     |     | 125 |     |     |     |
| Ala | Arg | Gly | Gly | Val | Leu | Val | Gly | Val | Gly | Ala | Ile | Val | Asp | Arg | Ser |
|     | 130 |     |     |     |     | 135 |     |     |     |     | 140 |     |     |     |     |
| Gly | Gly | Arg | Ala | Ala | Phe | Gly | Val | Pro | Phe | Arg | Ala | Leu | Leu | Ala | Leu |
| 145 |     |     |     |     | 150 |     |     |     |     | 155 |     |     |     |     | 160 |
| Glu | Val | Pro | Gln | Tyr | Pro | Glu | Glu | Ala | Cys | Pro | Leu | Cys | Arg | Glu | Gly |
|     |     |     |     | 165 |     |     |     |     | 170 |     |     |     |     | 175 |     |
| Val | Pro | Leu | Glu | Glu | Val |     |     |     |     |     |     |     |     |     |     |
|     |     |     | 180 |     |     |     |     |     |     |     |     |     |     |     |     |

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GAGCCATGGC CATTTAAAAA GGGAATGAG                29

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GAGGCCATGG TTCAAAATGG TATG                      24

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

AATCTAAAAT TATCTGAAAA GGGAATGAGA ATAGT          35

( 2 ) INFORMATION FOR SEQ ID NO:6:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:6:

CACTATTCTC ATTCCCTTTT CAGATAATTT TAGATT 36

( 2 ) INFORMATION FOR SEQ ID NO:7:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:7:

CATACCATTT TGAACGATGA CCTC 24

( 2 ) INFORMATION FOR SEQ ID NO:8:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:8:

GAGGTCATCG TTCAAAATGG TATG 24